United States Patent
Gouverneur et al.

(10) Patent No.: US 10,287,220 B2
(45) Date of Patent: May 14, 2019

(54) FLUORINATION METHOD

(71) Applicant: Oxford University Innovation Limited, Botley, Oxford (GB)

(72) Inventors: Veronique Gouverneur, Oxford (GB); Matthew Tredwell, Oxford (GB); Sean Preshlock, Oxford (GB)

(73) Assignee: Oxford University Innovation Limited, Botley, Oxford (GB)

( * ) Notice: Subject to any disclaimer, the term of this patent is extended or adjusted under 35 U.S.C. 154(b) by 0 days.

(21) Appl. No.: 15/127,599

(22) PCT Filed: Mar. 20, 2015

(86) PCT No.: PCT/GB2015/050831
§ 371 (c)(1),
(2) Date: Sep. 20, 2016

(87) PCT Pub. No.: WO2015/140572
PCT Pub. Date: Sep. 24, 2015

(65) Prior Publication Data
US 2017/0137341 A1    May 18, 2017

(30) Foreign Application Priority Data
Mar. 20, 2014 (GB) .................................. 1405002.5

(51) Int. Cl.
| | |
|---|---|
| C07D 295/16 | (2006.01) |
| C07B 59/00 | (2006.01) |
| C07F 5/04 | (2006.01) |
| C07C 17/361 | (2006.01) |
| C07C 37/62 | (2006.01) |
| C07C 41/22 | (2006.01) |
| C07C 45/65 | (2006.01) |
| C07C 67/317 | (2006.01) |
| C07C 201/12 | (2006.01) |
| C07C 209/74 | (2006.01) |
| C07C 231/12 | (2006.01) |
| C07C 253/30 | (2006.01) |
| C07C 303/40 | (2006.01) |
| C07D 209/08 | (2006.01) |
| C07D 215/18 | (2006.01) |
| C07D 277/30 | (2006.01) |
| C07D 295/073 | (2006.01) |
| C07F 5/02 | (2006.01) |

(52) U.S. Cl.
CPC ............ *C07B 59/002* (2013.01); *C07B 59/00* (2013.01); *C07B 59/001* (2013.01); *C07C 17/361* (2013.01); *C07C 37/62* (2013.01); *C07C 41/22* (2013.01); *C07C 45/65* (2013.01); *C07C 67/317* (2013.01); *C07C 201/12* (2013.01); *C07C 209/74* (2013.01); *C07C 231/12* (2013.01); *C07C 253/30* (2013.01); *C07C 303/40* (2013.01); *C07D 209/08* (2013.01); *C07D 215/18* (2013.01); *C07D 277/30* (2013.01); *C07D 295/073* (2013.01); *C07D 295/16* (2013.01); *C07F 5/025* (2013.01); *C07F 5/04* (2013.01); *C07B 2200/05* (2013.01); *Y02P 20/55* (2015.11)

(58) Field of Classification Search
CPC ..................................................... C07B 59/002
See application file for complete search history.

(56) References Cited

U.S. PATENT DOCUMENTS 3,090,801 A * 5/1963 Washburn ............... C07F 5/025
558/292

OTHER PUBLICATIONS

Ye, Journal of the American Chemical Society, 135(44), 16292-16295; 2013.*
Ye, J. Am. Chem. Soc. 2013, 135, 16292-16295.*
Stenhagen, Chemical Communications (Cambridge, United Kingdom) (2013), 49(14), 1386-1388.*
Roger, J Label Compd Radiopharm 2006; 49: 489-504.*
Fier, J. Am. Chem. Soc. 2013, 135, 2552-25.*
Talylor, J. Am. Chem. Soc. 2017, 139, 8267-8276.*
Tredwell, Angew.Chenn. Int. Ed. 2014, 53, 7751-7755, col. A, p. 7752-7753.*
Bergman, J., and O. Solin, "Fluorine-18-Labeled Fluorine Gas for Synthesis of Tracer Molecules," Nuclear Medicine and Biology 24(7):677-683, Oct. 1997.

(Continued)

*Primary Examiner* — Nizal S Chandrakumar
(74) *Attorney, Agent, or Firm* — Christensen O'Connor Johnson Kindness PLLC

(57) ABSTRACT

The present invention relates to a process for producing an organic compound comprising an $^{18}$F atom. The compounds comprising an $^{18}$F can be useful as PET ligands for use in diagnostics and/or scanning. The process of the invention comprises treating an organoboron compound, which organoboron compound comprises a boron atom bonded to an sp$^2$ hybridized carbon atom, with (i) $^{18}$F— and (ii) a copper compound. The invention also provides the use of an organoboron compound, which organoboron compound comprises a boron atom bonded to an sp$^2$ hybridized carbon atom, in a process for producing an organic compound comprising an $^{18}$F atom, which process comprises treating the organoboron compound with (i)$^{18}$F— and (ii) a copper compound. The invention also provides a compound of formula (XXXVII): wherein: each PG$^A$ is independently H or an alcohol protecting group; PG$^B$ is H or a carboxylic acid protecting group; each PG$^C$ is independently an amine protecting group; Z is a group selected from a boronic ester group, a boronic acid group, a borate group, and a trifluoroborate group; and a is an integer from 0 to 4.

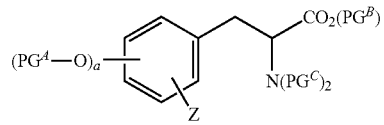

(XXXVII)

26 Claims, No Drawings

(56) References Cited

OTHER PUBLICATIONS

EMEA Committee for Human Medicinal Products (CHMP), "Guideline on the Specification Limits for Residues of Metal Catalysts (Draft)," Jan. 2007, London, <http://www.ema.europa.eu/docs/en_GB/document_library/Scientific_guideline/2009/09/WC500003587.pdf> [retrieved Jan. 25, 2017], 32 pages.

Fier, P.S., et al., "Copper-Mediated Fluorination of Arylboronate Esters. Identification of a Copper(III) Fluoride Complex," Journal of the American Chemical Society 135(7):2552-2559, Feb. 2013.

Gao, Z., et al., "Enhanced Aqueous Suzuki-Miyaura Coupling Allows Site-Specific Polypeptide $^{18}$F-Labeling," Journal of the American Chemical Socity 135(37):13612-13615, Sep. 2013.

Gao, Z., et al. "Metal-Free Oxidative Fluorination of Phenols With [$^{18}$F]Fluoride," Angewandte Chemie International Edition 51(27):6733-6737, Jul. 2012.

Hickman, A.J., and M.S. Sanford, "High-Valent Organometallic Copper and Palladium in Catalysis," Nature 484(7393):177-185, Apr. 2012.

Hitotsuyanagi, Y., et al., "Aza-Cycloisodityrosine Analogue of RA-VII, and Antitumor Bicyclic Hexapeptide," Bioorganic & Medicinal Chemistry Letters 23(24):6728-6731, Dec. 2013.

Huiban, M., et al., "A Broadly Applicable [$^{18}$F]trifluoromethylation of Aryl and Heteroaryl Iodides for PET Imaging," Nature: Chemistry 5(11):941-944, Nov. 2013.

Ichiishi, N., et al., "Copper-Catalysed [$^{18}$F]Fluorination of (Mesityl)(aryl)iodonium Salts," Organic Letters 16(12):3224-3227, Jun. 2014.

Kilitoglu, B., and H.-D. Arndt, "Thieme Chemistry Journal Awardees—Where are they Now? Scope of Tyrosine O-Arylations With Boronic Acids: Optimized Synthesis of an Orthogonally Protected Isodityrosine," Synlett 5:0720-0723, Mar. 2009.

Lee, E., et al. "A Fluoride-Derived Electrophilic Late-Stage Fluorination Reagent for PET Imaging," Science 334(6056):639-642, Nov. 2011.

Lee, E., et al., "Nickel-Mediated Oxidative Fluorination for PET with Aqueous [$^{18}$F]Fluoride," Journal of the American Chemical Society 134(42):17456-17458, Oct. 2012.

Liu, Z., et al., "Rapid, One-Step, High Yielding $^{18}$F-Labeling of an Aryltrifluoroborate Bioconjugate by Isotope Exchange at Very High Specific Activity," Journal of Labelled Compounds and Radiopharmaceuticals 55(14):491-496, Dec. 2012.

Makaravage, K.J., et al., "Copper-Mediated Radiofluorination of Arylstannanes With [$^{18}$F]KF," Organic Letters 18(20):5440-5443, Oct. 2016.

Miller, P.W., et al., "Synthesis of $^{11}$C, $^{18}$F, $^{15}$O, and $^{13}$N Radiolabels for Positron Emission Tomography," Angewandte Chemie International Edition 47(47):8998-9033, Nov. 2008.

Mossine, A.V., et al., "Synthesis of [$^{18}$F]Arenes via the Copper-Mediated [$^{18}$F]Fluorination of Boronic Acids," Organic Letters 17(23):5780-5783, Dec. 2015.

Muller, K., et al., "Fluorine in Pharmaceuticals: Looking Beyond Intuition," Science 317(5846):1881-1886, Sep. 2007.

Nakamura, H., et al., "A Practical Method for the Synthesis of Enantiomerically Pure 4-Borono-L-Phenylalanine," Bulletin of the Chemical Society of Japan 73(1):231-235, Jan. 2000.

Pike, V.W., and F.I. Aigbirhio, "Reactions of Cyclotron-Produced [18F]Fluoride With Diaryliodonium Salts—A Novel Single-Step Route to No-Carrier-Added [$^{18}$F]Fluoroarenes," Journal of the Chemical Society, Chemical Communications 21:2215-2216, 1995.

Preshlock, S., et al., "$^{18}$F-Labeling of Arenes and Heteroarenes for Applications in Positron Emission Tomography," Chemical Reviews 116(2):719-766, Jan. 2016.

Purser, S., et al., "Fluorine in Medicinal Chemistry," Chemical Society Reviews 37(2):320-330, Feb. 2008.

Shi, Z.-C., et al., "Modulation of Peripheral Serotonin Levels by Novel Tryptophan Hydroxyloase Inhibitors for the Potential Treatment of Functional Gastrointestinal Disorders," Journal of Medicinal Chemistry 51(13):3684-3687, Jul. 2008.

Stenhagen, I.S.R., et al., "[$^{18}$F]Fluorination of an Arylboronic Ester Using [$^{18}$F]selectfluor bis(triflate): Application to 6-[$^{18}$ $^{F}$]fluoro-L-DOPA," Chemical Communications 49(14):1386-1388, Feb. 2013.

Teare, H., et al., "Radiosynthesis and Evaluation of [$^{18}$F]Selectfluor bis(triflate)," Angewandte Chemie International Edition 49(38):6821-6824, Sep. 2010.

Tredwell, M., and V. Gouverneur, "$^{18}$F Labeling of Arenes," Angewandte Chemie International Edition 51(46):11426-11437, Nov. 2012.

Ye, Y., et al., "Cu(OTf)$_2$-Mediated Fluorination of Aryltrifluoroborates With Potassium Fluoride," Journal of the American Chemical Society 135(44):16292-16295, Nov. 2013.

Cardinale, et al., "Carrier-effect on palladium-catalyzed, nucleophilic 18F-fluorination of aryl triflates," J. Label Compd. Radiopharm. 2012, 55, 450-453, 4 pages.

Makaravage, et al., "Copper-Mediated Radiofluorination of Arylstannanes with [18F]KF," Org. Lett. 2016, 18, 5440-5443, 4 pages.

Mossine, et al., "Synthesis of [18F]Arenes via the Copper-Mediated [18F]Fluorination of Boronic Acids," Org. Lett. 2015, 17, 5780-5783, 4 pages.

Preshlock, et al., "Enhanced copper-mediated 18F-fluorination of aryl boronic esters provides eight radiotracers for PET applications," Chem. Commun. 2016, 52, 8361-8364, 5 pages.

Taylor, et al., "Derisking the Cu-Mediated 18F-Fluorination of Heterocyclic Positron Emission Tomography Radioligands," J. Am. Chem. Soc. 2017, 139, 8267-8276, 10 pages.

Tredwell, et al., "A General Copper-Mediated Nucleophilic 18F Fluorination of Arenes," Angew. Chem. Int. Ed. 2014, 53, 7751-7755, 5 pages.

Watson et al., "Formation of ArF from LPdAr(F): Catalytic Conversion of Aryl Triflates to Aryl Fluorides," Science, Sep. 2009, vol. 325, 6 pages.

* cited by examiner

FLUORINATION METHOD

FIELD OF THE INVENTION

The present invention relates to a process for producing an organic compound comprising an $^{18}$F atom. The compounds comprising an $^{18}$F can be useful as PET ligands for use in diagnostics and/or scanning. The invention also relates to the use of an organoboron compound in a process for producing an organic compound comprising an $^{18}$F atom. Organoboron compounds are also described.

BACKGROUND OF THE INVENTION

The first application of positron annihilation radiation for medical imaging followed by the development of the first human Positron Emission Tomography (PET) scanner were milestones in the deployment of PET imaging as we know it today. Further technological developments coupled with the appearance of radiopharmaceuticals, perhaps most notoriously [$^{18}$F]-2-fluorodeoxy-D-glucose, firmly established PET as a non-invasive imaging modality. Today PET is used routinely in the clinic to diagnose a range of cancers, neurological disorders and cardiovascular diseases. It has become a useful tool to facilitate drug discovery and development by enabling a new kind of precision pharmacology. These applications have created a demand for new radiochemistry with a focus on [$^{18}$F]fluorination, a choice driven by the advantageous properties of $^{18}$F as a positron emitter and the prevalence of fluorine substitution in drug design.

Molecules labelled with the unnatural isotope fluorine-18 are used as radiotracers for positron emission tomography. Typical challenges associated with $^{18}$F radiochemistry are the short half-life of $^{18}$F (<2 h), the use of sub-stoichiometric amounts of $^{18}$F, relative to the precursor and other reagents, as well as the limited availability of $^{18}$F sources of suitable reactivity ([18F]F$^-$ and [$^{18}$F]F$_2$). An important challenge in [$^{18}$F]radiochemistry is the labelling of (hetero)arenes not amenable to S$_N$Ar with ['T]F$^-$. In the ideal case, the [$^{18}$F] fluorination of these most demanding substrates would be performed with broadly used potassium [$^{18}$F]fluoride from shelf-stable readily available precursors applying a protocol amenable to automation.

In the past decade, the number of methods available for the installation of fluorine into (hetero)arenes has increased significantly since these structural motifs are commonly found in pharmaceutical drugs to impart metabolic robustness. In contrast, the preparation of [$^{18}$F]labeled (hetero) arenes that are not accessible via aromatic nucleophilic substitution with [$^{18}$F]fluoride remains challenging. The reaction of diaryliodonium salts with [18F]fluoride ions has been described almost 2 decades ago (V. W. Pike et al., Chem. Soc., Chem. Commun. 21, 2215 (1995)). Although it can be applied to labeling of electron-rich, electron neutral and electron-deficient arenes with fluorine-18, this reaction has gained limited interest due to significant limitations related to the tedious preparation of diaryliodonium salts and purification of aryl by-products. Recent advances exploit the value of metal-free umpolung strategies for the direct nucleophilic [$^{18}$F]fluorination of arenes under oxidative conditions, a concept successfully applied to phenol precursors (Z. Gao et al., Angew. Chem. Int. Ed. 51, 6733 (2012)). Metal-mediated processes have also emerged for direct [$^{18}$F]fluorination of various substrates inclusive of arenes not suitable for S$_N$Ar. Early studies demonstrated that the [$^{18}$F]NF reagent [$^{18}$F]Selectfluor bis(triflate) prepared from [$^{18}$F]F$_2$, allowed for the Ag(I)-mediated electrophilic [$^{18}$F] fluorination of arylstannannes (H. Teare et al., Angew. Chem. Int. Ed. 49, 6821 (2010)) and arylboronic acids (I. S. Stenhagen, A. K. Kirjavainen, S. J. Forsback, C. G. Jorgensen, E. G. Robins, S. K. Luthra, O. Solin, V. Gouverneur, Chem. Commun. 49, 1386 (2013)) within the time constraint imposed by the short half-life $^{18}$F isotope (t$_{1/2}$<2 h). Currently, this chemistry is not used broadly as only a minority of PET centers in the world is equipped to produce [$^{18}$F]F$_2$, and tracers derived from [$^{18}$F]F$_2$ are of lower specific activity than those produced from [$^{18}$F]fluoride. More recently, a purpose-built [$^{18}$F]Pd(IV)F complex prepared from high specific activity [$^{18}$F]F$^-$ but acting as a source of [$^{18}$F]F$^+$, converted Pd(II) aryl complexes, themselves obtained from the corresponding aryl boronic acids, into [$^{18}$F]fluoroarenes (E. Lee et al., Science 334, 639 (2011)). Ni(II) aryl complexes prepared in two steps from aryl bromides were also found amenable to nucleophilic [$^{18}$F] fluorination in the presence of an external oxidant, yielding a range of [$^{18}$F]labeled arenes in up to 58% radiochemical yield (RCY) (E. Lee, J. M. Hooker, T. Ritter, J. Am. Chem. Soc. 134, 17456 (2012)). These organometallic Pd- and Ni-based precursors are not commercially available and not trivial to prepare by non-chemist professionals performing (pre)clinical PET imaging studies. These characteristics coupled with the necessity to develop automated protocols in compliance with Good Manufacturing Practice (GMP) requirements, encourage the development of alternative simpler solutions for the direct nucleophilic [$^{18}$F]fluorination of (hetero)arenes from readily available shelf stable materials. Furthermore, there are toxicity concerns associated with the use of nickel and palladium.

As part of an ongoing research program in transition metal-promoted [$^{18}$F]fluorination, the inventors have previously exploited the value of copper complexes in [$^{18}$F] radiochemistry with the [$^{18}$F]trifluoromethylation of aryl and heteroaryl iodides from [$^{18}$F]CuCF$_3$ (M. Huiban et al., Nature Chemistry 5, 941 (2013)). It is desirable to develop a mild nucleophilic [$^{18}$F]fluorination of arylboron compounds with the aim to provide a general and simple method to access [$^{18}$F](hetero)arenes.

Recent reports disclosing aryl-fluoride bond forming reductive elimination reactions from high valency Cu$^{III}$ complexes provided a focus (A. J. Hickman, M. S. Sanford, Nature 484, 177 (2012)) and the ability of pinacol-derived arylboronate esters (ArBPin) to undergo fluorination with potassium fluoride in the presence of Cu(OTf)$_2$ served as a starting point for [$^{18}$F]radiochemical development (Y., Ye, S. D. Schimler, P. S. Hanley, M. S. Sanford, J. Am. Chem. Soc. 135, 16292 (2013)).

However, translation from the fluorination of Ye et al. to no-carrier added [$^{18}$F]radiochemistry presented several distinctive challenges. Firstly, since the "reverse stoichiometry" reflecting the minute quantities of fluorine (roughly 10$^{-4}$ M or lower) available for labeling contrasts with the necessity to use 4 equivalents of KF to achieve reasonable chemical yields of the desired fluoroarenes in Ye et al. it was not initially expected that the process could be used for radiolabelling. Complications could also arise from sequestration of [$^{18}$F]fluoride onto the boron-containing substrates used in excess. Thus, it is an object of the present invention to develop a [$^{18}$F]fluorination process which can be applied to a wide range of arene and heteroarene substrates while maintaining good radiochemical yields and specific activity.

SUMMARY OF THE INVENTION

The inventors have developed a process for producing an organic compound comprising an $^{18}$F atom. The process of the invention allows a nucleophilic source of $^{18}$F to be used which allows high specific activities to be obtained for the radiolabelled products. Furthermore, the process of the invention is broadly applicable to alkenes, arenes and heteroarenes which may be electron rich, electron neutral or electron deficient. The process may be used as a "no-carrier added" process as it can proceed with high radiochemical yield even at very low concentrations of $^{18}F$. This was unexpected from previous reports concerning Cu-mediated fluorination as large excesses of fluoride were typically required. The process of the invention opens simple, effective synthetic pathways for producing [$^{18}F$]radiolabelled PET biomarkers which were previously difficult to access. Importantly, the process of the invention can be used to produce [$^{18}F$]L-DOPA and other radiolabelled PET biomarkers. As the process of the invention tolerates the presence of a number of other functional groups and requires only mild conditions, it may be used in late stage fluorination of biomarker compounds, again leading to higher specific activities. Furthermore, The use of Cu salts is advantageous in comparison with transition metals such as Pd or Ni because Cu presents with lower safety concerns, and is therefore tolerated in higher residual amount in [$^{18}F$]tracers suitable for clinical studies.

Herein is described the production of [$^{18}F$](hetero)arenes and [$^{18}F$]biomarkers from organoboron compounds (for instance pinacol-derived aryl boronic esters) upon treatment with [$^{18}F$]fluoride and a copper compound. This [$^{18}F$]labelling method is compatible with many functional groups and allows direct access to PET ligands such as 6-[$^{18}F$]fluoro-L-DOPA, 6-[$^{18}F$]fluoro-L-tyrosine and 6-[$^{18}F$]fluoro-dopamine from [$^{18}F$]fluoride. Broad applications for drug development and (pre)clinical studies requiring Positron Emission Tomography imaging are now possible.

The inventors have developed an efficient no-carrier-added protocol that allows for facile [$^{18}F$]fluorination of aromatic systems with [$^{18}F$]fluoride from (hetero)aryl and alkenyl organoboron compounds. Organoboron reagents are ideal precursors for [$^{18}F$]fluorination as they are stable to air and moisture, and are stable on the bench. This technology tolerates a large range of functional groups, and may be readily applied to the successful radiosynthesis of the TSPO PET ligand [$^{18}F$] DAA1106, 6-[$^{18}F$]fluorotyrosine and 6-[$^{18}F$]Fluorodopamine. Clinical doses of 6-[$^{18}F$]fluoro-L-DOPA may be prepared in high radiochemical yield; this result suggests that this biomarker is now accessible from a bench stable precursor and a commercially available Cu complex in PET centers having the capacity to producing [$^{18}F$]FDG ([$^{18}F$]fludeoxyglucose). This novel [$^{18}F$]radiochemistry may find ample applications to facilitate biomarker and drug development, and previously unavailable $^{18}F$-PET tracers for clinical studies may also come within reach. The invention does not necessitate the preparation of complex diaryliodonium salts or organometallic precursors and can be performed with commercially available reagents in a reaction vessel exposed to air. Therefore, the process of the invention should be suitable for automated synthesizers and microfluidic development.

The invention provides a process for producing an organic compound comprising an $^{18}F$ atom, which process comprises treating an organoboron compound, which organoboron compound comprises a boron atom bonded to an $sp^2$ hybridised carbon atom, with
(i) $^{18}F^-$ and
(ii) a copper compound.

For instance, the invention provides a process for producing a compound of formula (XXIV):

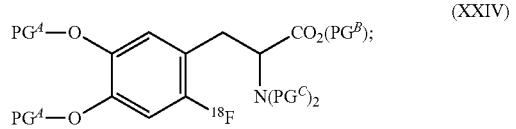

(XXIV)

which process comprises treating a compound of formula (XIX):

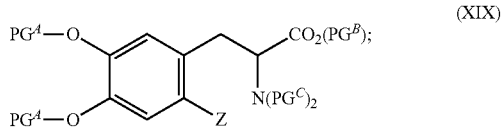

(XIX)

with
(i) $^{18}F^-$ and
(ii) a copper compound;
wherein:
each $PG^A$ is independently H or an alcohol protecting group;
$PG^B$ is H or a carboxylic acid protecting group; and
each $PG^C$ is independently H or an amine protecting group; and
Z is a group selected from a boronic ester group, a boronic acid group, a borate group, and a trifluoroborate group.

The invention also provides the use of an organoboron compound, which organoboron compound comprises a boron atom bonded to an $sp^2$ hybridised carbon atom, in a process for producing an organic compound comprising an $^{18}F$ atom, which process comprises treating said organoboron compound with
$^{18}F^-$ and
(ii) a copper compound.

The invention also provides a compound of formula (XXXVII):

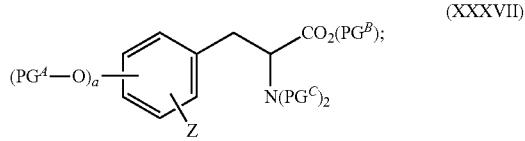

(XXXVII)

wherein:
each $PG^A$ is independently H or an alcohol protecting group;
$PG^B$ is H or a carboxylic acid protecting group;
each $PG^C$ is independently an amine protecting group;
Z is a group selected from a boronic ester group, a boronic acid group, a borate group, and a trifluoroborate group; and
a is an integer from 0 to 4.

DETAILED DESCRIPTION OF THE INVENTION

Definitions

The term "organoboron compound", as used herein, refers to an organic compound which comprises a C—B bond. The term "organic compound", as used herein, takes its normal meaning in the art.

The term "bonded to an $sp^2$ hybridised carbon", as used herein, takes its normal meaning in the art and thus refers to an atom which is bonded directly to a carbon atom which is $sp^2$ hybridised. An $sp^2$ hybridised carbon atom will typically have three atoms bonded to it in a planar arrangement. Examples of $sp^2$ hybridised carbon atoms are those which form part of a C=C double bond (or part of a bond which in some resonance structures is a C=C double bond, for instance in a benzene) or part of a C=N double bond. Thus a $sp^2$ hybridised carbon atom is typically a carbon atom in a C=C double bond, an aryl ring or a heteroaryl ring.

The term "alkyl group", as used herein, refers to an substituted or unsubstituted, straight or branched chain saturated hydrocarbon radical. Typically an alkyl group is $C_{1-20}$ alkyl, or $C_{1-10}$ alkyl, for example methyl, ethyl, propyl, butyl, pentyl, hexyl, heptyl, octyl, nonyl or decyl (including straight or branched chain isomers thereof), or $C_{1-6}$ alkyl, for example methyl, ethyl, propyl, butyl, pentyl or hexyl (including straight or branched chain isomers thereof), or $C_{1-4}$ alkyl, for example methyl, ethyl, i-propyl, n-propyl, t-butyl, s-butyl or n-butyl. When an alkyl group is substituted it typically bears one or more substituents selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, sulfonyl, phosphoric acid, phosphate ester, phosphonic acid and phosphonate ester. Examples of substituted alkyl groups include haloalkyl, hydroxyalkyl, aminoalkyl, alkoxyalkyl and alkaryl groups. The term alkaryl, as used herein, pertains to a $C_{1-20}$ alkyl group in which at least one hydrogen atom has been replaced with an aryl group. Examples of such groups include, but are not limited to, benzyl (phenylmethyl, $PhCH_2$—), benzhydryl ($Ph_2CH$—), trityl (triphenylmethyl, $Ph_3C$—), and phenethyl (phenylethyl, $Ph-CH_2CH_2$—). Typically a substituted alkyl group carries 1, 2 or 3 substituents, for instance 1 or 2.

The term "perfluoroalkyl", as used herein, refers to a group which is a straight or branched chain saturated perfluorinated hydrocarbon radical. For example, a perfluoroalkyl group may be have from a to 12 carbon atoms. "Perfluorinated" in this context means completely fluorinated such that there are no carbon-bonded hydrogen atoms replaceable with fluorine. Examples of $C_{4-12}$ perfluoro alkyl groups are trifluoromethyl ($C_1$), pentafluoroethyl ($C_2$), heptafluoropropyl ($C_3$), perfluorobutyl ($C_4$) (for instance including perfluoro-n-butyl, perfluoro-sec-butyl and perfluoro-tert-butyl), perfluoropentyl ($C_5$), perfluorohexyl ($C_6$), perfluoroheptyl ($C_7$), perfluorooctyl ($C_8$), perfluorononyl ($C_9$), perfluorodecyl ($C_{10}$), perfluoroundecyl ($C_{11}$) and perfluorododecyl ($C_{12}$), including straight chained and branched isomers thereof.

The term "alkenyl", as used herein, refers to a linear or branched chain hydrocarbon radical comprising one or more double bonds. An alkenyl group may be a $C_{2-20}$ alkenyl group, a $C_{2-10}$ alkenyl group or a $C_{2-6}$ alkenyl group. Examples of $C_{2-20}$ alkenyl groups include those related to $C_{2-20}$ alkyl groups by the insertion of one or more double bonds. Alkenyl groups typically comprise one or two double bonds. The alkenyl groups referred to herein may be substituted or unsubstituted, as defined for alkyl groups above.

The term "alkynyl", as used herein, refers to a linear or branched chain hydrocarbon radical comprising one or more triple bonds. An alkynyl group may be a $C_{2-20}$ alkynyl group, a $C_{2-10}$ alkynyl group a $C_{2-6}$ alkynyl group. Examples of $C_{2-20}$ alkynyl groups include those related to $C_{2-20}$ alkyl groups by the insertion of one or more triple bonds. Alkynyl groups typically comprise one or two triple bonds. The alkynyl groups referred to herein may be substituted or unsubstituted, as defined for alkyl groups above.

The term "cycloalkyl group", as used herein, refers to an substituted or unsubstituted alkyl group which is also a cyclyl group; that is, a monovalent moiety obtained by removing a hydrogen atom from an alicyclic ring atom of a carbocyclic ring of a carbocyclic compound. A cycloalkyl group may have from 3 to 25 carbon atoms (unless otherwise specified), including from 3 to 25 ring atoms. Thus, the term "cycloalkyl" includes the sub-classes cycloalkyenyl and cycloalkynyl. Examples of groups of $C_{3-25}$ cycloalkyl groups include $C_{3-20}$ cycloalkyl, $C_{3-15}$ cycloalkyl, $C_{3-10}$ cycloalkyl, and $C_{3-7}$ cycloalkyl. When a $C_{3-25}$ cycloalkyl group is substituted it typically bears one or more substituents selected from substituted or unsubstituted $C_{1-6}$ alkyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, phosphoric acid, phosphate ester, phosphonic acid and phosphonate ester and sulfonyl. Typically a substituted cycloalkyl group carries 1, 2 or 3 substituents, for instance 1 or 2.

Examples of $C_{3-25}$ cycloalkyl groups include, but are not limited to, those derived from saturated monocyclic hydrocarbon compounds, which $C_{3-25}$ cycloalkyl groups are substituted or unsubstituted as defined above: cyclopropane ($C_3$), cyclobutane ($C_4$), cyclopentane ($C_5$), cyclohexane ($C_6$), cycloheptane ($C_7$), methylcyclopropane ($C_4$), dimethylcyclopropane ($C_5$), methylcyclobutane ($C_5$), dimethylcyclobutane ($C_6$), methylcyclopentane ($C_6$), dimethylcyclopentane ($C_7$), methylcyclohexane ($C_7$), dimethylcyclohexane ($C_8$), menthane ($C_{10}$); unsaturated monocyclic hydrocarbon compounds: cyclopropene ($C_3$), cyclobutene ($C_4$), cyclopentene ($C_5$), cyclohexene ($C_6$), methylcyclopropene ($C_4$), dimethylcyclopropene ($C_5$), methylcyclobutene ($C_5$), dimethylcyclobutene ($C_6$), methylcyclopentene ($C_6$), dimethylcyclopentene ($C_7$), methylcyclohexene ($C_7$), dimethylcyclohexene ($C_8$); saturated polycyclic hydrocarbon compounds: thujane ($C_{10}$), carane ($C_{10}$), pinane ($C_{10}$), bornane ($C_{10}$), norcarane ($C_7$), norpinane ($C_7$), norbornane ($C_7$), adamantane ($C_{10}$), decalin (decahydronaphthalene) ($C_{10}$); unsaturated polycyclic hydrocarbon compounds: camphene ($C_{10}$), limonene ($C_{10}$), pinene ($C_{10}$); polycyclic hydrocarbon compounds having an aromatic ring: indene ($C_9$), indane (e.g., 2,3-dihydro-1H-indene) ($C_9$), tetraline (1,2,3,4-tetrahydronaphthalene) ($C_{10}$), acenaphthene ($C_{12}$), fluorene ($C_{13}$), phenalene ($C_{13}$), acephenanthrene ($C_{15}$), aceanthrene ($C_{16}$), cholanthrene ($C_{20}$).

The term "heterocyclyl group", as used herein, refers to an substituted or unsubstituted monovalent moiety obtained by removing a hydrogen atom from a ring atom of a heterocyclic compound, which moiety has from 3 to 20 ring atoms (unless otherwise specified), of which from 1 to 10 are ring heteroatoms. Heterocyclic compounds include aromatic heterocyclic compounds and non-aromatic heterocyclic compounds. Preferably, each ring has from 3 to 7 ring atoms, of which from 1 to 4 are ring heteroatoms. When a $C_{3-20}$ heterocyclyl group is substituted it typically bears one or more substituents selected from $C_{1-6}$ alkyl which is unsubstituted, aryl (as defined herein), cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, phosphoric acid, phosphate ester, phosphonic acid and phosphonate ester and sulfonyl. Typically a substituted $C_{3-20}$ heterocyclyl group carries 1, 2 or 3 substituents, for instance 1 or 2.

Examples of groups of heterocyclyl groups include $C_{3-20}$ heterocyclyl, $C_{5-20}$ heterocyclyl, $C_{3-15}$ heterocyclyl, $C_{5-15}$ heterocyclyl, $C_{3-12}$ heterocyclyl, $C_{5-12}$ heterocyclyl, $C_{3-10}$ heterocyclyl, $C_{5-10}$ heterocyclyl, $C_{3-7}$ heterocyclyl, $C_{5-7}$ heterocyclyl, and $C_{5-6}$ heterocyclyl.

Examples of (non-aromatic) monocyclic $C_{3-20}$ heterocyclyl groups include, but are not limited to, those derived from:
$N_1$: aziridine ($C_3$), azetidine ($C_4$), pyrrolidine (tetrahydropyrrole) ($C_5$), pyrroline (e.g., 3-pyrroline, 2,5-dihydropyrrole) ($C_5$), 2H-pyrrole or 3H-pyrrole (isopyrrole, isoazole) ($C_5$), piperidine ($C_6$), dihydropyridine ($C_6$), tetrahydropyridine ($C_6$), azepine ($C_7$);
$O_1$: oxirane ($C_3$), oxetane ($C_4$), oxolane (tetrahydrofuran) ($C_5$), oxole (dihydrofuran) ($C_5$), oxane (tetrahydropyran) ($C_6$), dihydropyran ($C_6$), pyran ($C_6$), oxepin ($C_7$);
$S_1$: thiirane ($C_3$), thietane ($C_4$), thiolane (tetrahydrothiophene) ($C_5$), thiane (tetrahydrothiopyran) ($C_6$), thiepane ($C_7$);
$O_2$: dioxolane ($C_5$), dioxane ($C_6$), and dioxepane ($C_7$);
$O_3$: trioxane ($C_6$);
$N_2$: imidazolidine ($C_5$), pyrazolidine (diazolidine) ($C_5$), imidazoline ($C_5$), pyrazoline (dihydropyrazole) ($C_5$), piperazine ($C_6$);
$N_1O_1$: tetrahydrooxazole ($C_5$), dihydrooxazole ($C_5$), tetrahydroisoxazole ($C_5$), dihydroisoxazole ($C_5$), morpholine ($C_6$), tetrahydrooxazine ($C_6$), dihydrooxazine ($C_6$), oxazine ($C_6$);
$N_1S_1$: thiazoline ($C_5$), thiazolidine ($C_5$), thiomorpholine ($C_6$);
$N_2O_1$: oxadiazine ($C_6$);
$O_1S_1$: oxathiole ($C_5$) and oxathiane (thioxane) ($C_6$); and,
$N_1O_1S_1$: oxathiazine ($C_6$).

Examples of substituted (non-aromatic) monocyclic heterocyclyl groups include those derived from saccharides, in cyclic form, for example, furanoses ($C_5$), such as arabinofuranose, lyxofuranose, ribofuranose, and xylofuranse, and pyranoses ($C_6$), such as allopyranose, altropyranose, glucopyranose, mannopyranose, gulopyranose, idopyranose, galactopyranose, and talopyranose.

Examples of $C_{3-20}$ heterocyclyl groups which are also aryl groups are described below as heteroaryl groups.

The term "aryl group", as used herein, refers to a substituted or unsubstituted, monocyclic or polycyclic (for instance bicyclic) aromatic group which typically contains from 6 to 14 carbon atoms, preferably from 6 to 10 carbon atoms in the ring portion. Examples include phenyl, naphthyl, indenyl, indanyl, anthracenyl and pyrenyl groups. An aryl group is substituted or unsubstituted. When an aryl group is substituted it typically bears one or more substituents selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, sulfonyl, phosphoric acid, phosphate ester, phosphonic acid and phosphonate ester. Typically it carries 0, 1, 2 or 3 substituents. A substituted aryl group may be substituted in two positions with a single $C_{1-6}$ alkylene group, or with a bidentate group represented by the formula —X—$C_{1-6}$ alkylene, or —X—$C_{1-6}$ alkylene-X—, wherein X is selected from O, S and NR, and wherein R is H, aryl or $C_{1-6}$ alkyl. Thus a substituted aryl group may be an aryl group fused with a cycloalkyl group or with a heterocyclyl group. The term "aralkyl" as used herein, pertains to an aryl group in which at least one hydrogen atom (e.g., 1, 2, 3) has been substituted with a $C_{1-6}$ alkyl group. Examples of such groups include, but are not limited to, tolyl (from toluene), xylyl (from xylene), mesityl (from mesitylene), and cumenyl (or cumyl, from cumene), and duryl (from durene).

The ring atoms of an aryl group may include one or more heteroatoms (as in a heteroaryl group). Such an aryl group is a heteroaryl group, and is a substituted or unsubstituted monocyclic or polycyclic (for instance bicyclic) heteroaromatic group which typically contains from 6 to 14 atoms, for instance 6 to 10 atoms, in the ring portion including one or more heteroatoms. It is generally a 5- or 6-membered ring, containing at least one heteroatom selected from O, S, N, P, Se and Si. It may contain, for example, 1, 2 or 3 heteroatoms. Examples of heteroaryl groups include pyridyl, pyrazinyl, pyrimidinyl, pyridazinyl, furanyl, thienyl, pyrazolidinyl, pyrrolyl, oxazolyl, oxadiazolyl, isoxazolyl, thiadiazolyl, thiazolyl, isothiazolyl, imidazolyl, pyrazolyl, quinolyl and isoquinolyl. A heteroaryl group may be substituted or unsubstituted, for instance, as specified above for aryl. Typically it carries 0, 1, 2 or 3 substituents.

The term "alkylene group" as used herein, refers to an substituted or unsubstituted bidentate moiety obtained by removing two hydrogen atoms, either both from the same carbon atom, or one from each of two different carbon atoms, of a hydrocarbon compound having from 1 to 20 carbon atoms (unless otherwise specified), which may be aliphatic or alicyclic, and which may be saturated, partially unsaturated, or fully unsaturated. Thus, the term "alkylene" includes the sub-classes alkenylene, alkynylene, cycloalkylene, etc., discussed below. Typically it is $C_{1-10}$ alkylene, for instance $C_{1-6}$ alkylene. Typically it is $C_{1-4}$ alkylene, for example methylene, ethylene, i-propylene, n-propylene, t-butylene, s-butylene or n-butylene. It may also be pentylene, hexylene, heptylene, octylene and the various branched chain isomers thereof. An alkylene group may be substituted or unsubstituted, for instance, as specified above for alkyl. Typically a substituted alkylene group carries 1, 2 or 3 substituents, for instance 1 or 2.

In this context, the prefixes (e.g., $C_{1-4}$, $C_{1-7}$, $C_{1-20}$, $C_{2-7}$, $C_{3-7}$, etc.) denote the number of carbon atoms, or range of number of carbon atoms. For example, the term "$C_{1-4}$alkylene," as used herein, pertains to an alkylene group having from 1 to 4 carbon atoms. Examples of groups of alkylene groups include $C_{1-4}$ alkylene ("lower alkylene"), $C_{1-7}$ alkylene, $C_{1-10}$ alkylene and $C_{1-20}$ alkylene.

Examples of linear saturated $C_{1-7}$ alkylene groups include, but are not limited to, —$(CH_2)_n$— where n is an integer from 1 to 7, for example, —$CH_2$— (methylene), —$CH_2CH_2$— (ethylene), —$CH_2CH_2CH_2$— (propylene), and —$CH_2CH_2CH_2CH_2$— (butylene).

Examples of branched saturated $C_{1-7}$ alkylene groups include, but are not limited to, —$CH(CH_3)$—, —$CH(CH_3)CH_2$—, —$CH(CH_3)CH_2CH_2$—, —$CH(CH_3)CH_2CH_2CH_2$—, —$CH_2CH(CH_3)CH_2$—, —$CH_2CH(CH_3)CH_2CH_2$—, —$CH(CH_2CH_3)$—, —$CH(CH_2CH_3)CH_2$—, and —$CH_2CH(CH_2CH_3)CH_2$—.

Examples of linear partially unsaturated $C_{1-7}$ alkylene groups include, but is not limited to, —CH=CH— (vinylene), —CH=CH—$CH_2$—, —$CH_2$—CH=$CH_2$—, —CH=CH—$CH_2$—$CH_2$—, —CH=CH—$CH_2$—$CH_2$—$CH_2$—, —$CH_2$—CH=CH—$CH_2$—, —CH=CH—CH=CH—, —CH=CH—CH=CH—$CH_2$—

CH$_2$—, —CH=CH—CH$_2$—CH=CH—, and —CH=CH—CH$_2$—CH$_2$—CH=CH—.

Examples of branched partially unsaturated C$_{1-7}$ alkylene groups include, but is not limited to, —C(CH$_3$)=CH—, —C(CH$_3$)=CH—CH$_2$—, and —CH=CH—CH(CH$_3$)—.

Partially unsaturated alkylene groups comprising one or more double bonds may be referred to as alkenylene groups. Partially unsaturated alkylene groups comprising one or more triple bonds may be referred to as alkynylene groups (for instance —C≡C—, CH$_2$—C≡C—, and —CH$_2$—C≡C—CH$_2$—).

Examples of alicyclic saturated C$_{1-7}$ alkylene groups include, but are not limited to, cyclopentylene (e.g., cyclopent-1,3-ylene), and cyclohexylene (e.g., cyclohex-1,4-ylene).

Examples of alicyclic partially unsaturated C$_{1-7}$ alkylene groups include, but are not limited to, cyclopentenylene (e.g., 4-cyclopenten-1,3-ylene), cyclohexenylene (e.g., 2-cyclohexen-1,4-ylene; 3-cyclohexen-1,2-ylene; 2,5-cyclohexadien-1,4-ylene).

C$_{1-20}$ alkylene and C$_{1-20}$ alkyl groups as defined herein are either uninterrupted or interrupted by one or more heteroatoms or heterogroups, such as S, O or N(R") wherein R" is H, C$_{1-6}$ alkyl or aryl (typically phenyl), or by one or more arylene (typically phenylene) groups, or by one or more —C(O)— or —C(O)N(R")— groups. The phrase "optionally interrupted" as used herein thus refers to a C$_{1-20}$ alkyl group or an alkylene group, as defined above, which is uninterrupted or which is interrupted between adjacent carbon atoms by a heteroatom such as oxygen or sulfur, by a heterogroup such as N(R") wherein R" is H, aryl or C$_1$-C$_6$ alkyl, or by an arylene group, or by a —C(O)— or —C(O)N(R")— group, again wherein R" is H, aryl or C$_1$-C$_6$ alkyl.

For instance, a C$_{1-20}$ alkyl group such as n-butyl may be interrupted by the heterogroup N(R") as follows: —CH$_2$N(R")CH$_2$CH$_2$CH$_3$, —CH$_2$CH$_2$N(R")CH$_2$CH$_3$, or —CH$_2$CH$_2$CH$_2$N(R")CH$_3$. Similarly, an alkylene group such as n-butylene may be interrupted by the heterogroup N(R") as follows: —CH$_2$N(R")CH$_2$CH$_2$CH$_2$—, —CH$_2$CH$_2$N(R")CH$_2$CH$_2$—, or —CH$_2$CH$_2$CH$_2$N(R")CH$_2$—. Typically an interrupted group, for instance an interrupted C$_{1-20}$ alkylene or C$_{1-20}$ alkyl group, is interrupted by 1, 2 or 3 heteroatoms or heterogroups or by 1, 2 or 3 arylene (typically phenylene) groups. More typically, an interrupted group, for instance an interrupted C$_{1-20}$ alkylene or C$_{1-20}$ alkyl group, is interrupted by 1 or 2 heteroatoms or heterogroups or by 1 or 2 arylene (typically phenylene) groups. For instance, a C$_{1-20}$ alkyl group such as n-butyl may be interrupted by 2 heterogroups N(R") as follows: —CH$_2$N(R")CH$_2$N(R")CH$_2$CH$_3$.

An arylene group is an substituted or unsubstituted bidentate moiety obtained by removing two hydrogen atoms, one from each of two different aromatic ring atoms of an aromatic compound, which moiety has from 5 to 14 ring atoms (unless otherwise specified). Typically, each ring has from 5 to 7 or from 5 to 6 ring atoms. An arylene group may be substituted or unsubstituted, for instance, as specified above for aryl.

In this context, the prefixes (e.g., C$_{5-20}$, C$_{6-20}$, C$_{5-14}$, C$_{5-7}$, C$_{5-6}$, etc.) denote the number of ring atoms, or range of number of ring atoms, whether carbon atoms or heteroatoms. For example, the term "C$_{5-6}$ arylene," as used herein, pertains to an arylene group having 5 or 6 ring atoms. Examples of groups of arylene groups include C$_{5-20}$ arylene, C$_{6-20}$ arylene, C$_{5-14}$ arylene, C$_{6-14}$ arylene, C$_{6-10}$ arylene, C$_{5-12}$ arylene, C$_{5-10}$ arylene, C$_{5-7}$ arylene, C$_{5-6}$ arylene, C$_5$ arylene, and C$_6$ arylene.

The ring atoms may be all carbon atoms, as in "carboarylene groups" (e.g., C$_{6-20}$ carboarylene, C$_{6-14}$ carboarylene or C$_{6-10}$ carboarylene).

Examples of C$_{6-20}$ arylene groups which do not have ring heteroatoms (i.e., C$_{6-20}$ carboarylene groups) include, but are not limited to, those derived from the compounds discussed above in regard to aryl groups, e.g. phenylene, and also include those derived from aryl groups which are bonded together, e.g. phenylene-phenylene (diphenylene) and phenylene-phenylene-phenylene (triphenylene).

Alternatively, the ring atoms may include one or more heteroatoms, as in "heteroarylene groups" (e.g., C$_{5-10}$ heteroarylene).

Examples of C$_{5-10}$ heteroarylene groups include, but are not limited to, those derived from the compounds discussed above in regard to heteroaryl groups.

As used herein the term "oxo" represents a group of formula: =O

As used herein the term "acyl" represents a group of formula: —C(=O)R, wherein R is an acyl substituent, for example, a substituted or unsubstituted C$_{1-20}$ alkyl group, substituted or unsubstituted C$_{2-20}$ alkenyl group, substituted or unsubstituted C$_{2-20}$ alkynyl group, a substituted or unsubstituted C$_{3-20}$ heterocyclyl group, a substituted or unsubstituted aryl group or a substituted or unsubstituted heteroaryl group, for instance a substituted or unsubstituted C$_{1-6}$ alkyl group. Examples of acyl groups include, but are not limited to, —C(=O)CH$_3$ (acetyl), —C(=O)CH$_2$CH$_3$ (propionyl), —C(=O)C(CH$_3$)$_3$ (t-butyryl), and —C(=O)Ph (benzoyl, phenone).

As used herein the term "acyloxy" (or reverse ester) represents a group of formula: —OC(=O)R, wherein R is an acyloxy substituent, for example, a substituted or unsubstituted C$_{1-20}$ alkyl group, substituted or unsubstituted C$_{2-20}$ alkenyl group, substituted or unsubstituted C$_{2-20}$ alkynyl group, a substituted or unsubstituted C$_{3-20}$ heterocyclyl group, a substituted or unsubstituted aryl group or a substituted or unsubstituted heteroaryl group, for instance a substituted or unsubstituted C$_{1-6}$ alkyl group. Examples of acyloxy groups include, but are not limited to, —OC(=O)CH$_3$ (acetoxy), —OC(=O)CH$_2$CH$_3$, —OC(=O)C(CH$_3$)$_3$, —OC(=O)Ph, and —OC(=O)CH$_2$Ph.

As used herein the term "ester" (or carboxylate, carboxylic acid ester or oxycarbonyl) represents a group of formula: —C(=O)OR, wherein R is an ester substituent, for example, a substituted or unsubstituted C$_{1-20}$ alkyl group, substituted or unsubstituted C$_{2-20}$ alkenyl group, substituted or unsubstituted C$_{2-20}$ alkynyl group, a substituted or unsubstituted C$_{3-20}$ heterocyclyl group, a substituted or unsubstituted aryl group or a substituted or unsubstituted heteroaryl group, for instance a substituted or unsubstituted C$_{1-6}$ alkyl group. Examples of ester groups include, but are not limited to, —C(=O)OCH$_3$, —C(=O)OCH$_2$CH$_3$, —C(=O)OC(CH$_3$)$_3$, and —C(=O)OPh.

As used herein the term "amino" represents a group of formula —NH$_2$. The term "C$_1$-C$_{10}$ alkylamino" represents a group of formula —NHR' wherein R' is a C$_{1-10}$ alkyl group, preferably a C$_{1-6}$ alkyl group, as defined previously. The term "di(C$_{1-10}$)alkylamino" represents a group of formula —NR'R" wherein R' and R" are the same or different and represent C$_{1-10}$ alkyl groups, preferably C$_{1-6}$ alkyl groups, as defined previously. The term "arylamino" represents a group of formula —NHR' wherein R' is an aryl group, preferably a phenyl group, as defined previously. The term "diarylamino" represents a group of formula —NR'R" wherein R' and R" are the same or different and represent aryl groups, preferably phenyl groups, as defined previously. The term "arylalkylamino" represents a group of formula —NR'R" wherein R' is a $C_{1-10}$ alkyl group, preferably a $C_{1-6}$ alkyl group, and R" is an aryl group, preferably a phenyl group.

A halo group is chlorine, fluorine, bromine or iodine (a chloro group, a fluoro group, a bromo group or an iodo group). It is typically chlorine, fluorine or bromine.

As used herein the term "amido" represents a group of formula: —C(=O)NR'R", wherein R' and R" are independently amino substituents, as defined for di($C_{1-10}$)alkylamino groups. Examples of amido groups include, but are not limited to, —C(=O)NH$_2$, —C(=O)NHCH$_3$, —C(=O)N(CH$_3$)$_2$, —C(=O)NHCH$_2$CH$_3$, and —C(=O)N(CH$_2$CH$_3$)$_2$, as well as amido groups in which R' and R", together with the nitrogen atom to which they are attached, form a heterocyclic structure as in, for example, piperidinocarbonyl, morpholinocarbonyl, thiomorpholinocarbonyl, and piperazinocarbonyl.

As used herein the term "acylamido" represents a group of formula: —NR$^1$C(=O)R$^2$, wherein R$^1$ is an amide substituent, for example, hydrogen, a $C_{1-20}$alkyl group, a $C_{3-20}$ heterocyclyl group, an aryl group, preferably hydrogen or a $C_{1-20}$ alkyl group, and R$^2$ is an acyl substituent, for example, a $C_{1-20}$ alkyl group, a $C_{3-20}$ heterocyclyl group, or an aryl group, preferably hydrogen or a $C_{1-20}$ alkyl group. Examples of acylamide groups include, but are not limited to, —NHC(=O)CH$_3$, —NHC(=O)CH$_2$CH$_3$, —NHC(=O)Ph, —NHC(=O)C$_{15}$H$_{31}$ and —NHC(=O)C$_9$H$_{19}$. Thus, a substituted $C_{1-20}$ alkyl group may comprise an acylamido substituent defined by the formula —NHC(=O)—$C_{1-20}$ alkyl, such as —NHC(=O)C$_{15}$H$_{31}$ or —NHC(=O)C$_9$H$_{19}$. R$^1$ and R$^2$ may together form a cyclic structure, as in, for example, succinimidyl, maleimidyl, and phthalimidyl:

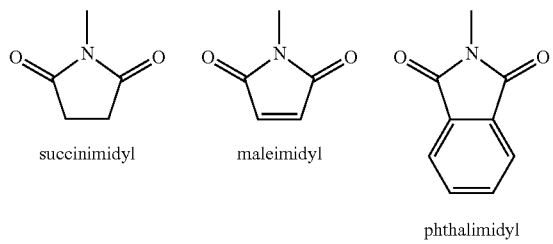

A $C_{1-10}$ alkylthio group is a said $C_{1-10}$ alkyl group, preferably a $C_{1-6}$ alkyl group, attached to a thio group. An arylthio group is an aryl group, preferably a phenyl group, attached to a thio group.

A $C_{1-20}$ alkoxy group is a said substituted or unsubstituted $C_{1-20}$ alkyl group attached to an oxygen atom. A $C_{1-6}$ alkoxy group is a said substituted or unsubstituted $C_{1-6}$ alkyl group attached to an oxygen atom. A $C_{1-4}$ alkoxy group is a substituted or unsubstituted $C_{1-4}$ alkyl group attached to an oxygen atom. Said $C_{1-20}$, $C_{1-6}$ and $C_{1-4}$ alkyl groups are optionally interrupted as defined herein. Examples of $C_{1-4}$ alkoxy groups include, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy). Further examples of $C_{1-20}$ alkoxy groups are —O(Adamantyl), —O—CH$_2$-Adamantyl and —O—CH$_2$—CH$_2$-Adamantyl. An aryloxy group is a substituted or unsubstituted aryl group, as defined herein, attached to an oxygen atom. An example of an aryloxy group is —OPh (phenoxy).

Unless otherwise specified, included in the above are the well known ionic, salt, solvate, and protected forms of these substituents. For example, a reference to carboxylic acid or carboxyl group (—COOH) also includes the anionic (carboxylate) form (—COO$^-$), a salt or solvate thereof, as well as conventional protected forms. Similarly, a reference to an amino group includes the protonated form (—N$^+$HR$^1$R$^2$), a salt or solvate of the amino group, for example, a hydrochloride salt, as well as conventional protected forms of an amino group. Similarly, a reference to a hydroxyl group also includes the anionic form (—O$^-$), a salt or solvate thereof, as well as conventional protected forms.

Certain compounds may exist in one or more particular geometric, optical, enantiomeric, diastereomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

Note that, except as discussed below for tautomeric forms, specifically excluded from the term "isomers," as used herein, are structural (or constitutional) isomers (i.e., isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g., $C_{1-7}$alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto, enol, and enolate forms, as in, for example, the following tautomeric pairs: keto/enol (illustrated below), imine/enamine, amide/imino alcohol, amidine/amidine, nitroso/oxime, thioketone/enethiol, N-nitroso/hyroxyazo, and nitro/aci-nitro.

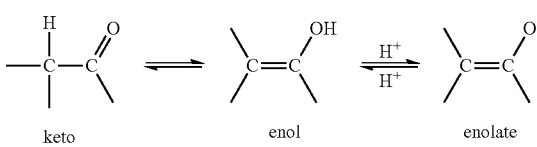

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, and $^{13}$C, $^{14}$C; O may be in any isotopic form, including $^{16}$O and $^{18}$O; and the like, unless otherwise specified. However, reference to an isotope of fluorine refers only to that isotope of fluorine. In particular, reference to $^{18}$F includes only $^{18}$F. Reference to fluorine without specifying the isotope may refer to $^{18}$F or $^{19}$F depending on context. Typically, reference to "F" (i.e. without defining the isotope) refers to the $^{19}$F, i.e. stable fluorine.

Unless otherwise specified, a reference to a particular compound includes all such isomeric forms, including (wholly or partially) racemic and other mixtures thereof.

Methods for the preparation (e.g., asymmetric synthesis) and separation (e.g., fractional crystallisation and chromatographic means) of such isomeric forms are either known in the art or are readily obtained by adapting known methods, in a known manner.

The term "substituted", as used herein, may be as defined above for particular groups. However, in some instances, the term substituted may refer to a group substituted with a group selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-20}$ alkoxy, aryloxy, haloalkyl, sulfonic acid, sulfhydryl (i.e. thiol, —SH), $C_{1-10}$ alkylthio, arylthio, sulfonyl, phosphoric acid, phosphate ester, phosphonic acid and phosphonate ester. In other instances, the term "substituted" may refer to a group substituted with a group selected from substituted or unsubstituted $C_{1-6}$ alkyl, substituted or unsubstituted $C_{2-6}$ alkenyl, substituted or unsubstituted $C_{2-6}$ alkynyl, substituted or unsubstituted aryl, substituted or unsubstituted heteroaryl, cyano, amino, $C_{1-6}$ alkylamino, di($C_{1-6}$)alkylamino, arylamino, diarylamino, arylalkylamino, amido, acylamido, hydroxy, oxo, halo, carboxy, ester, acyl, acyloxy, $C_{1-6}$ alkoxy, aryloxy, haloalkyl, sulfonic acid, thiol, $C_{1-6}$ alkylthio, arylthio, sulfonyl, phosphoric acid, phosphate ester, phosphonic acid and phosphonate ester. For example, the term "substituted" may refer to a group substituted with a group selected unsubstituted $C_{1-6}$ alkyl, unsubstituted $C_{2-6}$ alkenyl, unsubstituted $C_{2-6}$ alkynyl, unsubstituted aryl, unsubstituted heteroaryl, cyano, amino, unsubstituted $C_{1-6}$ alkylamino, unsubstituted di($C_{1-6}$)alkylamino, unsubstituted arylamino, unsubstituted diarylamino, unsubstituted arylalkylamino, unsubstituted amido, unsubstituted acylamido, hydroxy, oxo, halo, carboxy, unsubstituted ester, unsubstituted acyl, unsubstituted acyloxy, unsubstituted $C_{1-6}$ alkoxy, unsubstituted aryloxy, sulfonic acid, thiol, unsubstituted $C_{1-6}$ alkylthio, unsubstituted arylthio, sulfonyl, phosphoric acid, unsubstituted phosphate ester, unsubstituted phosphonic acid and unsubstituted phosphonate ester.

The term "$^{18}$F" refers to an atom of the specific isotope of fluorine having 9 protons and 9 neutrons. The term "$^{18}$F$^-$" refers to an anion of the atom of the specific isotope of fluorine having 9 protons and 9 neutrons.

The term "boronic ester group", as used herein, refers to a group of formula —B(OR)$_2$ wherein R is H or an organic group, for instance a substituted or unsubstituted alkyl group. The term "boronic acid group", as used herein, refers to a group of formula —B(OH)$_2$. The term "borate group", as used herein, refers to a group of formula —B(OR)$_3^-$ wherein R is H or an organic group, for instance a substituted or unsubstituted alkyl group. As borate groups are negatively charged, a cation is typically present, for instance a metal cation such as Na$^+$ or K$^+$. The term "trifluoroborate group", as used herein, refers to a group of formula —BF$_3^-$. As trifluoroborate groups are negatively charged, a cation is typically present, for instance a metal cation such as Na$^+$ or K$^+$.

The term "ligand", as used herein, refers to a species capable of binding to a central atom (in this case a copper atom or ion) to form a complex. Ligands may be charged or neutral species. Typically, as referred to herein, a ligand is a neutral species.

The term "halide", as used herein, refers to fluoride, chloride, bromide and iodide.

The term "protecting group", as used herein, takes its normal meaning in the art. Thus, a protecting group is a group which is introduced into a compound so that a subsequent step is chemoselective and does not affect the protected group. Protecting groups may be categorised as those suitable for protecting specific functional groups. Thus a protecting group may, for instance, be an alcohol protecting group, an amine protecting group or a carboxylic acid protecting group.

Process

The invention provides a process for producing an organic compound comprising an $^{18}$F atom, which process comprises treating an organoboron compound, which organoboron compound comprises a boron atom bonded to an sp$^2$ hybridised carbon atom, with $^{18}$F$^-$ and (ii) a copper compound.

Typically the organoboron compound is treated with both (i) and (ii) simultaneously. Thus, typically the process comprises treating the organoboron compound with $^{18}$F$^-$ in the presence of the copper compound. Equivalently, the process may comprise treating the organoboron compound with the copper compound in the presence of $^{18}$F$^-$. $^{18}$F$^-$ may refer to any suitable source of $^{18}$F$^-$, as discussed below. Often $^{18}$F$^-$ will be solvated.

The organoboron usually contains only one boron atom. The organoboron compound typically comprises a boronic ester group, a boronic acid group, a borate group or a trifluoroborate group. Often, the organoboron compound comprises a boronic ester group. The boron atom of said groups are bonded to an sp$^2$ hybridised carbon atom. Thus, the boronic ester group, boronic acid group, borate group or trifluoroborate group is typically bonded to a carbon atom in a C=C double bond or a carbon atom in an aryl or heteroaryl ring. The organoboron compound may be an alkenylboronic ester compound, an alkenylboronic acid compound, an arylboronic ester compound, or an arylboronic acid compound. In one embodiment, the organoboron compound is an arylboronic ester compound.

Copper Compound

Any suitable copper compound may be used in the process of the invention. The copper compound is often a copper salt. The copper salt may be a copper (I) salt, a copper (II) salt, or a copper (III) salt. Preferably, the copper compound is a copper (II) salt or a copper (III) salt. More preferably, the copper compound is a copper (II) salt. The copper compound may be a simple salt comprising Cu$^{n+}$ (n=1, 2, or 3) and one or more anions or may be a salt comprising a complex copper cation and one or more cations. Thus, the copper compound may be a copper salt comprising one or more X groups, wherein each X group is the same or different and is an anion. For instance the copper compound may be a salt of formula CuX$_2$, where X is an anion and the salt may further comprise one or more neutral ligands.

In one embodiment, the copper compound comprises a compound of formula [L$_n$CuX$_m$], wherein: each L is the same or different and is a ligand, optionally wherein two or more L groups are bonded together to form one or more rings; each X is the same or different and is an anion, optionally wherein two or more X groups are bonded together to form one or more rings; n is an integer from 0 to 6; and m is an integer from 0 to 4. Often the copper compound is a compound of formula [L$_n$CuX$_m$].

The compound of formula [L$_n$CuX$_m$] may be charged or neutral. Thus it may be a complex copper cation. If the compound of formula [L$_n$CuX$_m$] is charged, the copper compound may further comprise one or more counterions. For instance, if the compound of formula [L$_n$CuX$_m$] is positively charged, the copper compound may further comprise one or more anions. The one or more anions may be selected from any anion described herein. The one or more anions may be selected from halide, hydroxide, sulfate, and nitrate. The copper complex may be cationic or anionic, and associated with one or more counter-ions. The copper compound may for instance be cationic, and associated with one or more counter-anions. The compound of formula [L$_n$-CuX$_m$] may be a monocation, a dication, or a trication for example. Any suitable counter-anion may be employed; a wide range of suitable counter anions is well known to the skilled person. The counter-anion or -anions may for instance be selected from halide, hydroxide, sulfate, nitrate, hexafluorophosphate, chlorate or tetrafluoroborate anions. Alternatively, the metal complex may be anionic, and associated with one or more counter-cations. Again, any suitable counter-cation may be employed; many such cations are known to the skilled person.

In the formula [L$_n$CuX$_m$], the copper atom Cu may be a neutral copper atom or a copper (I), (II) or (III) ion. Often, formula [L$_n$CuX$_m$] comprises a Cu(II) ion.

n is often an integer from 0 to 4, for instance 3 or 4. m is typically an integer from 1 to 3, for instance 2.

In the formula [L$_n$CuX$_m$], one or more of the L groups is often a ligand comprising one or more N atoms, one or more O atoms or one or more S atoms. Examples of ligands comprising one or more N atoms include ammonia, an alkylamine, a dialkylamine, a trialkylamine, an arylamine, a diarylamine, a triarylamine, an alkylenediamine and a heterocyclic compound comprising one or more N atoms. Alky, aryl, alkylene and heterocyclic groups in ligands comprising one or more N atoms may be as described anywhere herein, and such groups may be unsubstituted. Examples of ligands comprising one or more O atoms include water, an alcohol, a carboxylic acid (including a carboxylate), a dialkylether, an alkylenediol and a heterocyclic compound comprising one or more O atoms. An alcohol ligand may be a compound of formula ROH wherein R is a substituted or unsubstituted alkyl compound as described anywhere herein. A carboxylic acid ligand may be a compound of formula RCOOH or RCOO$^-$ wherein R is a substituted or unsubstituted alkyl group as described anywhere herein. Alkyl, alkylene and heterocyclic groups in ligands comprising one or more O atoms may be as described anywhere herein. Examples of ligands comprising one or more S atoms include H$_2$S, a alkylthiol, a dialkylthio ether and a heterocyclic compound comprising one or more S atoms. Alkyl and heterocyclic groups in ligands comprising one or more S atoms may be as described anywhere herein.

Often, one or more of the L groups is a neutral ligand selected from a heterocyclic compound comprising one or more N atoms, a heterocyclic compound comprising one or more O atoms, a heterocyclic compound comprising one or more S atoms, an amine, and water. Examples of heterocyclic compounds comprising one or more N atoms include aziridine, azetidine, pyrrolidine (tetrahydropyrrole), pyrroline (e.g., 3-pyrroline, 2,5-dihydropyrrole), 2H-pyrrole or 3H-pyrrole (isopyrrole, isoazole), piperidine, dihydropyridine, tetrahydropyridine, azepine, imidazolidine, pyrazolidine (diazolidine), imidazoline, pyrazoline (dihydropyrazole), piperazine, tetrahydrooxazole, dihydrooxazole, tetrahydroisoxazole, dihydroisoxazole, morpholine, tetrahydrooxazine, dihydrooxazine, oxazine, thiazolidine, thiomorpholine, oxadiazine, pyridine, pyrazine, pyrimidine, pyridazine, pyrazolidine, pyrrole, oxazole, isoxazole, thiadiazole, thiazolyl, isothiazole, imidazole, pyrazole, quinoline, isoquinoline, oxadiazole, phenanthroline and 2,2'-bipyridyl. Examples of heterocyclic compounds comprising one or more O atoms include oxirane, oxetane, oxolane (tetrahydrofuran), oxole (dihydrofuran), oxane (tetrahydropyran), dihydropyran, pyran, oxepin, dioxolane, dioxane, dioxepane, trioxane, tetrahydrooxazole, dihydrooxazole, tetrahydroisoxazole, dihydroisoxazole, morpholine, tetrahydrooxazine, dihydrooxazine, oxazine, oxadiazine, oxathiole, oxathiane (thioxane), oxathiazine, a saccharide, furan, oxazole, oxadiazole, and isoxazole. Examples of heterocyclic compounds comprising one or more S atoms include thiophene, tetrahydrothiophene, thiazole, isothiazole, thiazoline, dithiane, and thiomorpholine. The amine may be ammonia, an alkylamine, a dialkylamine, a trialkylamine, an arylamine, a diarylamine, a triarylamine, or an alkylenediamine.

In one embodiment, one or more of the L groups is a ligand selected from substituted or unsubstituted pyridine, substituted or unsubstituted pyrrole, substituted or unsubstituted pyrrolidine, substituted or unsubstituted imidazole, substituted or unsubstituted imidazoline, substituted or unsubstituted imidazolidine, substituted or unsubstituted pyrazole, substituted or unsubstituted pyrazoline, substituted or unsubstituted pyrazolidine, substituted or unsubstituted pyrazoline, substituted or unsubstituted oxazole, substituted or unsubstituted isoxazole, substituted or unsubstituted thiazole, and substituted or unsubstituted isothiazole, or wherein two of the L groups are bonded together to form a ligand selected from substituted or unsubstituted C$_{1-6}$ alkylene diamine, substituted or unsubstituted 2,2'-bipyridine, and substituted or unsubstituted phenanthroline. For instance, one or more of the L groups may be a ligand selected from substituted or unsubstituted pyridine, substituted or unsubstituted 2,2'-bipyridine, and substituted or unsubstituted phenanthroline. Often, one or more of the L groups is substituted or substituted pyridine.

In one embodiment, one or more of the L groups is a ligand of formula (I)

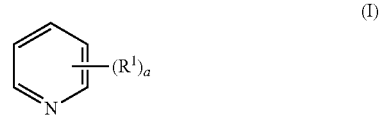

wherein: each R$^1$ is the same or different and is a substituent selected from substituted or unsubstituted C$_{1-10}$ alkyl, substituted or unsubstituted C$_{2-10}$ alkenyl, substituted or unsubstituted C$_{2-10}$ alkynyl, substituted or unsubstituted C$_{3-10}$ cycloalkyl, substituted or unsubstituted heterocyclyl, substituted or unsubstituted aryl, substituted or unsubstituted heteroaryl, cyano, amino, C$_{1-10}$ alkylamino, di(C$_{1-10}$)alkylamino, arylamino, diarylamino, arylalkylamino, amido, acylamido, hydroxy, halo, carboxy, ester, acyl, acyloxy, C$_{1-10}$ alkoxy, aryloxyaloalkyl, sulfonic acid, thiol, C$_{1-10}$ alkylthio, arylthio, sulfonyl, phosphoric acid, phosphate ester, phosphonic acid and phosphonate ester; and a is an integer from 0 to 5.

For example, R$^1$ may be selected from unsubstituted C$_{1-6}$ alkyl, unsubstituted C$_{2-6}$ alkenyl, unsubstituted C$_{2-6}$ alkynyl, unsubstituted aryl, unsubstituted heteroaryl, cyano, amino, unsubstituted C$_{1-6}$ alkylamino, unsubstituted di(C$_{1-6}$)alkylamino, unsubstituted arylamino, unsubstituted diarylamino, unsubstituted arylalkylamino, unsubstituted amido, unsubstituted acylamido, hydroxy, oxo, halo, carboxy, unsubstituted ester, unsubstituted acyl, unsubstituted acyloxy, unsubstituted $C_{1-6}$ alkoxy, unsubstituted aryloxy, sulfonic acid, thiol, unsubstituted $C_{1-6}$ alkylthio, unsubstituted arylthio, sulfonyl, phosphoric acid, unsubstituted phosphate ester, unsubstituted phosphonic acid and unsubstituted phosphonate ester. Thus, $R^1$ may be selected from unsubstituted $C_{1-6}$ alkyl. a is often 0, 1 or 2.

Often, one or more of the L groups is unsubstituted pyridine. For instance, every L group may be unsubstituted pyridine.

As described above, the copper compound is often a copper salt comprising one or more anions X. Often, one or more of the X groups is an anion selected from halide anions and anions of formula $[-OS(O)_2Y]^-$, $[-S(O)_2Y]^-$, and $[-OC(O)Y^-]$, wherein Y is a group selected from halide, substituted or unsubstituted $C_{1-10}$ alkyl, substituted or unsubstituted $C_{2-10}$ alkenyl, substituted or unsubstituted $C_{2-10}$ alkynyl, perfluoroalkyl, substituted or unsubstituted $C_{3-10}$ cycloalkyl groups, substituted or unsubstituted aryl groups and substituted or unsubstituted heterocyclyl groups. For instance, Y may be methyl, benzyl, toluenyl, or perfluoroalkyl. Y may be a perfluoroalkyl group selected from trifluoromethyl, pentafluoroethyl, heptafluoropropyl, perfluorobutyl (including perfluoro-n-butyl, perfluoro-sec-butyl and perfluoro-tert-butyl), perfluoropentyl, perfluorohexyl, perfluoroheptyl, perfluorooctyl, perfluorononyl, perfluorodecyl, perfluoroundecyl and perfluorododecyl, including straight chained and branched isomers thereof.

Preferably, one or more of the X groups is an anion selected from triflate (—OTf), triflyl (-Tf), nonaflate, fluorosulfonate, sulfonate, tosyl, mesylate, pivalate, acetate, trifluoroacetate, fluoride, chloride, bromide, iodide, and hydroxide. One or more of the X groups may be an anion selected from triflate (—OTf), triflyl (-Tf), nonaflate, fluorosulfonate, sulfonate, tosyl, mesylate, pivalate, acetate, trifluoroacetate, chloride, bromide, iodide, and hydroxide. For example, one or more of the X groups may be selected from triflate, nonaflate, fluorosulfonate, sulfonate, and tosyl. Preferably, each X is an anion of formula $[-OS(O)_2Y]^-$ wherein Y is F or perfluoroalkyl. For instance, each X may be triflate.

The copper compound may be a compound of formula $[L_nCu(OTf)_2]$, wherein each L is the same or different and is a ligand, optionally wherein two or more L groups are bonded together to form one or more rings; n is an integer from 0 to 4. L may as defined anywhere herein, for instance substituted or unsubstituted pyridine. n is often an integer from 2 to 4, for instance 4.

In one embodiment, the copper compound is a compound of formula $[(Py)_4Cu^{II}(OTf)_2]$. Here "Py" represents unsubstituted pyridine.

In some instances, an additive may also be present in the reaction. This additive may be a salt, for instance a carbonate salt, a hydrogencarbonate salt or a phosphate salt, or water. For instance, the additive may be caesium carbonate $(Cs_2CO_3)$, tetraethylammonium hydrogencarbonate $(Et_4NHCO_3)$ or potassium phosphate $(K_3PO_4)$.

A Brønsted acid may be present as an additive. For instance, a pyridinium compound, such as a pyridinium triflate or a pyridinium sulfonate compound, may be present during the reaction. Examples of pyridinium triflates include di-tert-butyl pyridinium triflate and pyridinium triflate. Examples of pyridinium sulfonates include pyridinium phenylsulfonate and pyridinium toluenesulfonate.

An oxidant may also be present during the reaction. If an oxidant is present, the oxidant may be any suitable oxidant. The oxidant may be selected from oxygen, hydrogen peroxide, organic peroxides, organic peroxyacids, oxidant metal salts and benzoquinones.

Organoboron Compound

The organoboron compound treated in the process of the invention comprises a boron atom bonded to an $sp^2$ hybridised carbon atom, as discussed above. Typically, therefore, the organoboron compound is a compound of formula (II) or (III):

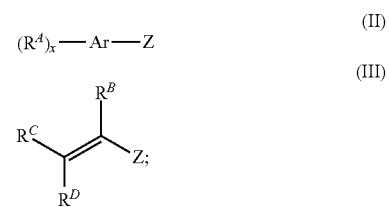

wherein:
Ar is an aryl ring or a heteroaryl ring;
each $R^A$ group is the same or different and is a group selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{3-20}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, aryloxy, haloalkyl, sulfonic acid, thiol, $C_{1-10}$ alkylthio, arylthio, sulfonyl, phosphoric acid, phosphate ester, phosphonic acid and phosphonate ester, wherein two or more $R^A$ groups may be bonded together to form one or more rings;
$R^B$, $R^C$, and $R^D$ are each independently selected from H, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{3-20}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, aryloxy, haloalkyl, sulfonic acid, thiol, $C_{1-10}$ alkylthio, arylthio, sulfonyl, phosphoric acid, phosphate ester, phosphonic acid and phosphonate ester, wherein two or more of $R^B$, $R^C$, and $R^D$ may be bonded together to form one or more rings;
Z is group selected from a boronic ester group, a boronic acid group, a borate group or a trifluoroborate group; and
x is an integer from 0 to 5.

For instance, each $R^A$ group may be independently selected from substituted or unsubstituted $C_{1-10}$ alkyl, substituted or unsubstituted $C_{1-10}$ alkenyl, substituted or unsubstituted $C_{1-10}$ alkynyl, substituted or unsubstituted $C_{3-10}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, and aryloxy, wherein two or more $R^A$ groups may be bonded together to form one or more rings. Each $R^A$ group may, for instance, be independently selected from substituted or unsubstituted $C_{1-10}$ alkyl, substituted or unsubstituted $C_{3-10}$ cycloalkyl, substituted or unsubstituted heterocyclyl, substituted or unsubstituted aryl, substituted or unsubstituted heteroaryl, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, and aryloxy, wherein two or more $R^A$ groups may be bonded together to form one or more rings. When two or more $R^A$ groups bond together to form one or more rings, the two or more $R^A$ groups may form an alkylene group as described herein, for instance a substituted or unsubstituted $C_{2-6}$ alkylene group which may be optionally interrupted as described herein.

$R^B$, $R^C$, and $R^D$ are often each independently selected from H, substituted or unsubstituted $C_{1-10}$ alkyl, substituted or unsubstituted $C_{1-10}$ alkenyl, substituted or unsubstituted $C_{1-10}$ alkynyl, substituted or unsubstituted $C_{3-10}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, and aryloxy, wherein two or more of $R^B$, $R^C$, and $R^D$ may be bonded together to form one or more rings. $R^B$, $R^C$, and $R^D$ may, for instance, be independently selected from H and substituted or unsubstituted $C_{1-10}$ alkyl, substituted or unsubstituted $C_{3-10}$ cycloalkyl, substituted or unsubstituted heterocyclyl, substituted or unsubstituted aryl, substituted or unsubstituted heteroaryl, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, and aryloxy, wherein two or more of $R^B$, $R^C$, and $R^D$ may be bonded together to form one or more rings. When two or more $R^B$, $R^C$, and $R^D$ bond together to form one or more rings, the two or more of $R^B$, $R^C$, and $R^D$ may form an alkylene group as described herein, for instance a substituted or unsubstituted $C_{2-6}$ alkylene group which may be optionally interrupted as described herein.

Z may be a group of formula (IV):

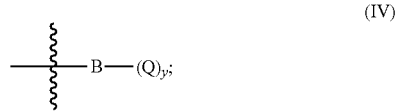

wherein:
each Q is the same or different and is a group selected from —$OR^E$, —OH, and fluoride;
each $R^E$ is the same or different and is a group selected from substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, substituted or unsubstituted heteroaryl, acyl, ester, amido, and haloalkyl, wherein two or more $R^E$ groups may be bonded together to form one or more rings; and
y is 2 or 3.

$R^E$ may be selected from substituted or unsubstituted $C_{1-10}$ alkyl, wherein two or more $R^E$ groups may be bonded together to form one or more rings. For instance, two $R^E$ groups may together form a substituted or unsubstituted $C_{1-10}$ alkylene group as described herein.

Z is often a group of formula —$B(OR^E)_2$. Thus, Z is often a boronic ester group. Z is often a cyclic boronic ester group. For example, Z may be a group of formula (V):

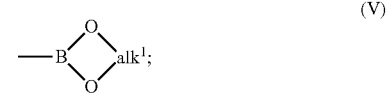

wherein alk¹ is a substituted or unsubstituted alkylene group, optionally interrupted with one or more —O— or —N($R^F$)— groups, wherein $R^F$ is a group selected from H, substituted or unsubstituted $C_{1-10}$ alkyl, acyl, ester, amido and acyloxy. Often, alk¹ is a substituted or unsubstituted $C_{1-10}$ alkylene group, optionally interrupted with one —O— or —N($R^F$)— groups, wherein $R^F$ is a group selected from H, substituted or unsubstituted $C_{1-10}$ alkyl, acyl, ester, amido and acyloxy. alk¹ may be a substituted or unsubstituted $C_{2-5}$ alkylene group which is uninterrupted.

For example, Z may be a group of formula (VI) or (VII):

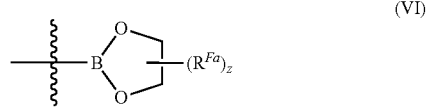

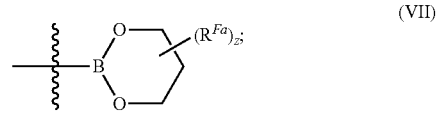

wherein: each $R^{Fa}$ is independently a group selected from substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, oxo, halo, carboxy, ester, acyl, acyloxy, $C_{1-10}$ alkoxy, aryloxy, haloalkyl, sulfonic acid, thiol, $C_{1-10}$ alkylthio, arylthio, sulfonyl, phosphoric acid, phosphate ester, phosphonic acid and phosphonate ester; and z is an integer from 0 to 6.

In formula (VI) and (VII), each $R^{Fa}$ may be bonded to any one of the alkylene carbon atoms bridging the two O atoms. Each $R^{Fa}$ may be a group independently selected from substituted or unsubstituted $C_{1-10}$ alkyl groups. For example, $R^{Fa}$ may be methyl or ethyl.

Often, Z is a group selected from

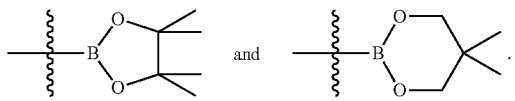

Thus, Z may be a pinacol boronic ester or a neopentyl glycol boronic ester.

In formula (II), Ar is an aryl ring or a heteroaryl ring. For instance Ar is often a ring selected from aryl rings such as phenyl, naphthenyl, anthracenyl and pyrenyl, and from heteroaryl rings such as pyridinyl, pyridonyl, pyrimidinyl, pyrimidonyl, pyrimidinedionyl, pyrrolyl, oxazolyl, thiazolyl, and imidazolyl. Ar is often a ring selected from phenyl, pyridinyl, pyridonyl, pyrimidinyl, pyrimidonyl, pyrimidinedionyl, pyrrolyl, oxazolyl, thiazolyl, and imidazolyl. For instance, Ar may be a ring selected from phenyl, pyridinyl, pyridonyl, pyrimidinyl, pyrimidonyl, and pyrimidinedionyl. Often, Ar is a ring selected from phenyl and pyridinyl.

In one embodiment, the organoboron compound is a compound of formula (VIII), (IX), (X), or (XI):

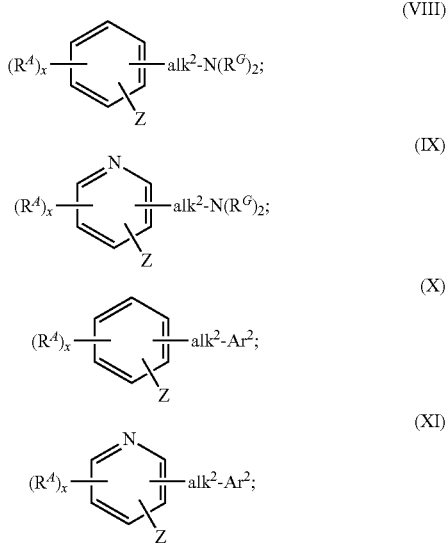

wherein:
- $Ar^2$ is a substituted or unsubstituted aryl group or a substituted or unsubstituted heteroaryl group; $alk^2$ is single bond or a substituted or unsubstituted $C_{1-20}$ alkylene group, a substituted or unsubstituted $C_{2-20}$ alkenylene group, a substituted or unsubstituted $C_{2-20}$ alkynylene group, wherein $alk^2$ may be optionally interrupted with one or more —O— or —N($R^F$)— groups, wherein $R^F$ is a group selected from H, substituted or unsubstituted $C_{1-10}$ alkyl, acyl, ester, and amido;
- each $R^A$ group is the same or different and is a group selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{3-20}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, aryloxy, haloalkyl, sulfonic acid, thiol, $C_{1-10}$ alkylthio, arylthio, sulfonyl, phosphoric acid, phosphate ester, phosphonic acid and phosphonate ester, or two or more $R^A$ groups may be bonded together to form one or more rings;
- each $R^G$ is the same or different and is group selected from H, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{3-20}$ cycloalkyl, substituted or unsubstituted heterocyclyl, substituted or unsubstituted aryl, substituted or unsubstituted heteroaryl, ester, acylamido, acyl, and acyloxy, or both $R^G$ groups together form a substituted or unsubstituted heterocyclyl group or a substituted or unsubstituted heteroaryl group;
- x is an integer from 0 to 4;
- and Z is as defined in anywhere herein.

$Ar^2$ may be as described herein for Ar. For instance, $Ar^2$ may be a group selected from phenyl, pyridinyl, pyridonyl, pyrimidinyl, pyrimidonyl, pyrimidinedionyl, and thiazolyl, which may be substituted or unsubstituted. Often, $Ar^2$ is a ring selected from phenyl, pyridinyl and thiazolyl.

$alk^2$ is often a single bond or a substituted or unsubstituted $C_{1-10}$ alkylene group, a substituted or unsubstituted $C_{2-10}$ alkenylene group, a substituted or unsubstituted $C_{2-10}$ alkynylene group, wherein $alk^2$ may be optionally interrupted with one or more —O— or —N($R^F$)— groups, wherein $R^F$ is a group selected from H, substituted or unsubstituted $C_{1-10}$ alkyl, acyl, ester, and amido. For instance $alk^2$ may be selected from a single bond, methyl, ethyl, vinyl, ethynyl and —CH$_2$N($R^F$)—.

$R^A$ may be as further defined above for the organoboron compound of formula (II).

Often, each $R^G$ is the same or different and is group selected from substituted or unsubstituted $C_{2-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, substituted or unsubstituted heteroaryl, ester, acylamido, amido, acyl, and acyloxy, or both $R^G$ groups together form a substituted or unsubstituted heterocyclyl group or a substituted or unsubstituted heteroaryl group. For instance, $R^G$ may be selected from ester, amido and acyl. $R^G$ is often an amine protection group, such as those discussed herein (for instance Boc or Fmoc).

x is often an integer from 0 to 3, for instance 1 or 2.

Z may be as defined in anywhere herein. For instance, Z may be a boronic ester as defined anywhere herein, for instance as defined in formulae (IV), (V), (VI) or (VII). Often, Z is a boronic pinacol ester.

The process of the invention allows access with good radiochemical yield to hitherto hard-to-reach radiolabelled biomarkers. In particular, the process of the invention may be used to produce 6-[$^{18}$F]fluoro-L-DOPA, 6-[$^{18}$F]fluoro-L-tyrosine, 6-[$^{18}$F]fluoro-dopamine, N-[(2,5-dimethoxyphenyl)methyl]-N-(5-[18F]fluoro-2-phenoxy-phenyl)acetamide, [$^{18}$F]3-fluoro-5-((2-methylthiazol-4-yl)ethynyl)benzonitrile, and [$^{18}$F]flutemetamol (typically in a protected form). In one embodiment, the process of the invention is a process for producing a PET ligand or a protected form thereof.

Several useful PET ligands have structures related to those set out in formulae (XII) to (XVI) below. Thus, in one embodiment, the organoboron compound is a compound of formula (XII), (XIII), (XIV), (XV) or (XVI):

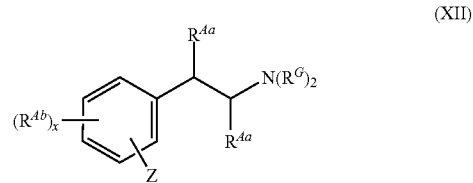

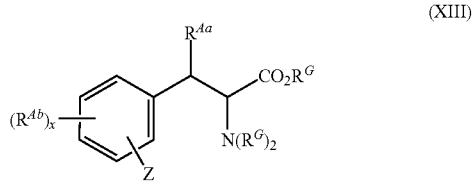

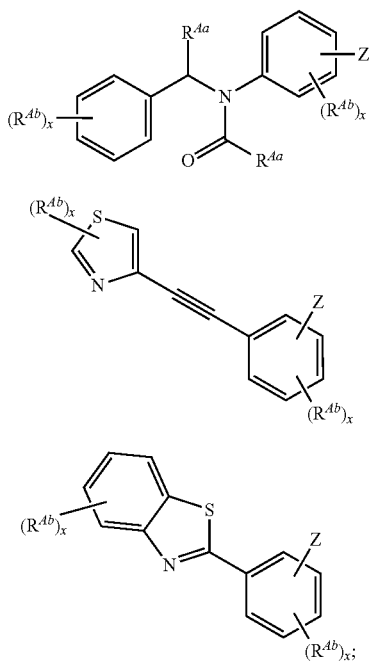

wherein:
each $R^M$ group is the same or different and is a group selected from H, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{3-20}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, aryloxy, haloalkyl, sulfonic acid, thiol, $C_{1-10}$ alkylthio, arylthio, sulfonyl, phosphoric acid, phosphate ester, phosphonic acid and phosphonate ester, wherein two or more $R^M$ groups may be bonded together to form one or more rings;

each $R^{Ab}$ group is the same or different and is a group selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{3-20}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, aryloxy, haloalkyl, sulfonic acid, thiol, $C_{1-10}$ alkylthio, arylthio, sulfonyl, phosphoric acid, phosphate ester, phosphonic acid and phosphonate ester, wherein two or more $R^{Ab}$ groups may be bonded together to form one or more rings;

each $R^G$ is the same or different and is group selected from H, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{3-20}$ cycloalkyl, substituted or unsubstituted heterocyclyl, substituted or unsubstituted aryl, substituted or unsubstituted heteroaryl, acylamido, acyl, and acyloxy, or both $R^G$ groups together form a substituted or unsubstituted heterocyclyl group or a substituted or unsubstituted aryl group;

each x is independently an integer from 0 to 4; and
Z is as defined anywhere herein.

Often, each $R^{Aa}$ group is the same or different and is a group selected from H, substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, and aryloxy, wherein two or more $R^{Aa}$ groups may be bonded together to form one or more rings. Typically, $R^{Aa}$ is H.

Each $R^{Ab}$ group may be the same or different and may be a group selected from substituted or unsubstituted $C_{1-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, and aryloxy, wherein two or more $R^{Ab}$ groups may be bonded together to form one or more rings.

Often, each $R^G$ is the same or different and is group selected from substituted or unsubstituted $C_{2-10}$ alkyl, substituted or unsubstituted $C_{2-10}$ alkenyl, substituted or unsubstituted $C_{2-10}$ alkynyl, substituted or unsubstituted $C_{3-10}$ cycloalkyl, substituted or unsubstituted heterocyclyl, substituted or unsubstituted aryl, substituted or unsubstituted heteroaryl, ester, acylamido, amido, acyl, and acyloxy, or both $R^G$ groups together form a substituted or unsubstituted heterocyclyl group or a substituted or unsubstituted heteroaryl group. For instance, $R^G$ may be selected from ester, amido and acyl. $R^G$ may be an amine protecting group as discussed herein, for instance Boc or Fmoc.

Each x may be, for example, an integer from 0 to 3, for instance 0, 1 or 2.

Z may be as defined anywhere herein. Often Z is a boronic ester group.

Often, the organoboron compound is a compound of formula (XVII) or (XVIII):

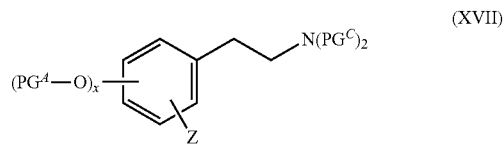

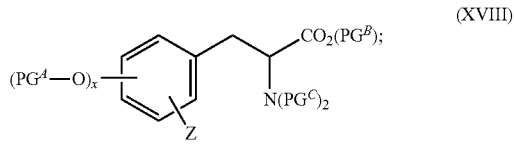

wherein:
each $PG^A$ is independently H or an alcohol protecting group;
$PG^B$ is H or a carboxylic acid protecting group;
each $PG^C$ is independently H or an amine protecting group;
x is an integer from 0 to 4; and
Z is as defined anywhere herein.

For example, the organoboron compound may be a compound of formula (XIX), (XX) or (XXI):

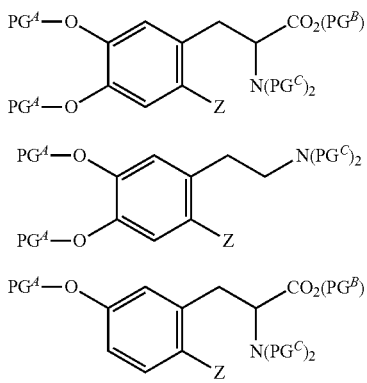

wherein:
each $PG^A$ is independently H or an alcohol protecting group;
$PG^B$ is H or a carboxylic acid protecting group;
each $PG^C$ is independently H or an amine protecting group; and
Z is as defined anywhere herein.

For example: $PG^A$ may independently be an alcohol protecting group; $PG^B$ may be a carboxylic acid protecting group; and each $PG^C$ may independently be an amine protecting group.

Typically, each $PG^A$ is independently H or an alcohol protecting group selected from substituted or unsubstituted $C_{1-10}$ alkyl, substituted or unsubstituted —C(O)—$C_{1-10}$ alkyl, substituted or unsubstituted —$C_{1-10}$ alkylene-O—$C_{1-10}$ alkyl optionally wherein the $C_{1-10}$ alkylene group and $C_{1-10}$ alkyl group may be bonded together to form a ring, and substituted or unsubstituted tri($C_{1-10}$ alkyl) silyl.

Typically, $PG^B$ is H or a carboxylic acid protecting group selected from substituted or unsubstituted $C_{1-10}$ alkyl, substituted or unsubstituted —C(O)—$C_{1-10}$ alkyl, and substituted or unsubstituted tri($C_{1-10}$ alkyl) silyl.

Typically, each $PG^C$ is independently H or an amine protecting group selected from substituted or unsubstituted $C_{1-10}$ alkyl, substituted or unsubstituted —C(O)—$C_{1-10}$ alkyl, substituted or unsubstituted —C(O)—O—$C_{1-10}$ alkyl, and substituted or unsubstituted —S(O)$_2$— aryl.

There are a wide range of protecting groups which are well known to the skilled person. Often, each $PG^A$ is independently H or a group selected from methyl, ethyl, tert-butyl, benzyl, p-methoxybenzyl, trityl, acetyl, benzoyl, pivaloyl, methoxymethyl, methoxyethoxymethyl, methoxytrityl, dimethoxytrityl, tetrahydrofuranyl, tetrahydropyranyl, trimethylsilyl, tert-butyldimethylsilyl, tri-iso-propyl silyloxymethyl, and tri-iso-propylsilyl; $PG^B$ is H or a group selected from methyl, ethyl, tert-butyl, benzyl, p-methoxybenzyl, trityl, trimethylsilyl, tert-butyldimethylsilyl, tri-iso-propyl silyloxymethyl, and tri-iso-propylsilyl; and each $PG^C$ is independently H or a group selected from carbobenzyloxy (Cbz), p-methoxybenzyl carbonyl (Moz), tert-butyloxycarbonyl (Boc), 9-fluorenylmethyloxycarbonyl (FMOC), acetyl, benzoyl, benzyl, p-methoxybenzyl (PMB), 3,4-dimethoxybenzyl (DMPM), p-methoxyphenyl (PMP), tosyl (Ts) and Nosyl (2- or 4-nitrobenzensulfonyl).

For instance, each $PG^A$ may be independently H or a group selected methyl, ethyl, tert-butyl, and benzyl; $PG^B$ may be group selected from methyl, ethyl, tert-butyl, and benzyl; and each $PG^C$ may be independently H or a group selected from carbobenzyloxy (Cbz), p-methoxybenzyl carbonyl (Moz), tert-butyloxycarbonyl (Boc), 9-fluorenylmethyloxycarbonyl (FMOC), acetyl, benzoyl, and benzyl.

The organoboron compound may be a compound of formula (XXII), (XXIII), (XXIIA) or (XXIIIA).

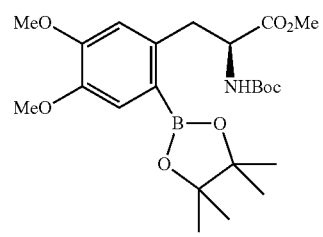

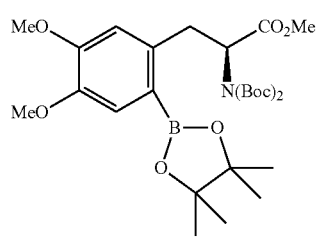

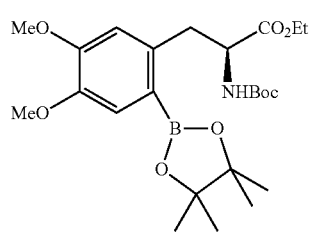

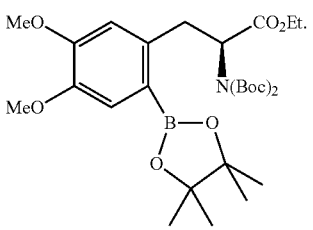

Process Conditions

The amount of the copper compound may be any suitable amount. The ratio of the amount of the organoboron compound to the amount of the copper compound may be from 1:40 to 40:1, for instance from 1:20 to 20:1. Typically, the amount of the copper compound is less than the amount of the organoboron compound. The ratio of the amount of the organoboron compound to the amount of the copper compound is typically from 1:1 to 40:1, preferably from 3:1 to 20:1. For instance, the ratio of the amount of the organoboron compound to the amount of the copper compound may be from 5:1 to 15:1.

The process of the invention is typically carried out in solution. The process may be carried out in solution in any suitable solvent. Typically the solvent is a polar aprotic solvent. For instance, the process may be carried out in the presence of a solvent selected polar aprotic solvents. Polar aprotic solvents are well known to the skilled person. The process may be carried out in the presence of a solvent selected from dimethyl formamide, N,N-dimethyl acetamide and acetonitrile. Often the process may be carried out in a mixture of solvents, for instance dimethyl formamide and acetonitrile.

The organoboron compound, the copper compound and the $^{18}F^-$ are typically heated to a temperature of from 80 to 150° C. For instance, the reactants may be heated to a temperature of from 100 to 120° C. The reagents may be heated for a length of time from 1 minute to 1 hour, for instance from 10 minutes to 30 minutes.

Often, the process according to the invention comprises:
(a) mixing the organoboron compound, the copper compound, the $^{18}F^-$ and a polar aprotic solvent;
(b) heating the resulting mixture to at a temperature of from 80 to 150° C. for from 10 to 30 minutes; and
(c) optionally quenching the reaction by addition of a polar protic solvent, for instance water.

Often (b) comprises heating the resulting mixture in a sealed container. The components and steps in this process may be as described anywhere herein.

The $^{18}F^-$ used in the process of the invention may be in any suitable form. Typically, the $^{18}F^-$ is present as a salt. Thus, the process of the invention may comprise treating the organoboron compound with (i) a salt of $^{18}F^-$ and (ii) said copper compound. Typically the concentration of $^{18}F^-$ is less than or equal to $10^{-4}$ M, for instance less than or equal to $10^{-5}$ M. In some cases, the concentration of $^{18}F^-$ will be nanomolar or less, for instance less than or equal to $10^{-8}$ M. $^{19}F^-$ may also be present. In such a case, the total fluoride concentration (including $^{18}F^-$ and $^{19}F^-$) may be less than or equal to $10^{-4}$ M, for instance less than or equal to $10^{-5}$ M.

Any suitable source of $^{18}F^-$ may be used. As will be understood by the skilled person the $^{18}F^-$ will typically be present in the form of a salt, with a counter cation. Any suitable counter cation may be used. Typically, the counter cation is a quaternary ammonium cation, for instance tetrabutylammonium, or an alkali metal cation, for instance $Cs^+$ or $K^+$, or a proton, $H^+$. Typically, when an alkali metal cation is employed, the alkali metal is cation complexed in a cryptand, for instance aminopolyether 2.2.2 ($K_{222}$), which is commercially available as Kryptofix-222. Advantageously, the addition of such a cryptand enables the fluoride ion $^{18}F^-$ to be solubilized in a polar aprotic solvent, for instance acetonitrile or DMF. It also enables the formation of a 'naked fluoride ion' as a KF—$K_{222}$ complex. In one embodiment, therefore, the source of $^{18}F^-$ is a K[$^{18}F$]F—$K_{222}$ complex. Alternatively, the source of $^{18}F^-$ may be [$^{18}F$]TEAF (tetraethylammonium fluoride), [$^{18}F$]TBAF (tetrabutylammonium fluoride), [$^{18}F$]CsF, or [$^{18}F$]HF. Typically, $^{18}F^-$ is present as K[$^{18}F$]F—$K_{222}$ or [$^{18}F$]HF. More typically, $^{18}F^-$ is present as K[$^{18}F$]F—$K_{222}$.

The process may be performed under any suitable atmosphere. For instance, the process may be performed under an inert atmosphere such as nitrogen or argon, or the process may be performed in the presence of oxygen, for instance in air. Often, the process is performed in air.

Compound Comprising an $^{18}F$ Atom

The organic compound comprising an $^{18}F$ atom may be a compound of formula (II), (III), (VIII), (IX), (X), (XI), (XII), (XIII), (XIV), (XV), (XVI), (XVII), (XVIII), (XIX), (XX), (XXI), (XXII) or (XXIII) as defined anywhere above, except wherein Z is replaced with $^{18}F$.

Often, the organic compound comprising an $^{18}F$ atom is a PET ligand or a protected form thereof. The PET ligand may be protected with one or more of the protecting groups described herein. For instance, the organic compound comprising an $^{18}F$ atom may be 6-[$^{18}F$]fluoro-L-DOPA, 6-[$^{18}F$]fluoro-L-tyrosine, 6-[$^{18}F$]fluoro-dopamine, N-[(2,5-dimethoxyphenyl)methyl]-N-(5-[18F]fluoro-2-phenoxy-phenyl)acetamide, [$^{18}F$]3-fluoro-5-((2-methylthiazol-4-yl)ethynyl)benzonitrile, or [$^{18}F$]flutemetamol, or a protected form thereof. Examples of PET ligands are well known to the skilled person. PET ligands are those compounds which are suitable for use in PET imaging. PET ligands may also be referred to as PET radiotracers. PET ligands are suitable for use in PET imaging.

In one embodiment, the organic compound comprising an $^{18}F$ atom is a compound of formula (XXIV), (XXV), (XXVI), (XXVII), or (XXVIII):

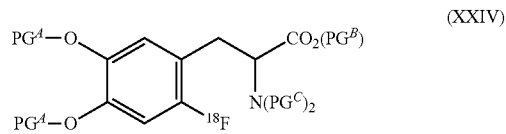

(XXIV)

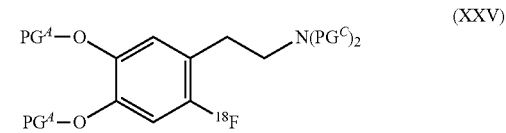

(XXV)

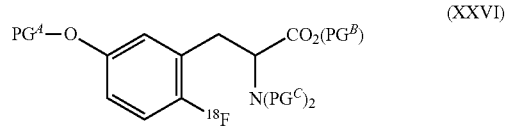

(XXVI)

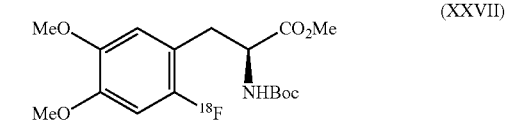

(XXVII)

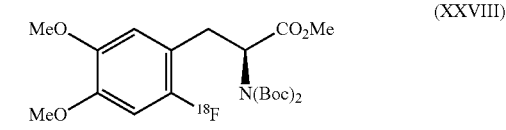

(XXVIII)

wherein
each $PG^A$ is independently H or an alcohol protecting group;
$PG^B$ is H or a carboxylic acid protecting group; and
each $PG^C$ is independently H or an amine protecting group.

$PG^A$, $PG^B$ and $PG^C$ may be as defined anywhere herein. For instance, each $PG^A$ may be independently H or a group selected methyl, ethyl, tert-butyl, and benzyl; $PG^B$ may be group selected from methyl, ethyl, tert-butyl, and benzyl; and each $PG^C$ may be independently H or a group selected from carbobenzyloxy (Cbz), p-methoxybenzyl carbonyl (Moz), tert-butyloxycarbonyl (Boc), 9-fluorenylmethyloxycarbonyl (FMOC), acetyl, benzoyl, and benzyl.

As mentioned above, the compound comprising an $^{18}F$ atom is often in a protected form. Thus, the process often further comprises a step of removing one or more protecting groups from the compound comprising an $^{18}F$ atom to produce a deprotected product. Removing one of more protecting groups from the compound comprising the $^{18}F$ atom may be referred to as a deprotection step. A deprotection may be performed by any suitable method. Such methods are well known to the skilled person. Often, removing one or more protecting groups from the compound comprising an $^{18}F$ atom comprises performing hydrolysis on the compound. For instance, the process may further comprise treating the compound comprising an $^{18}F$ atom with an aqueous acid, for instance aqueous HI, HBr or HCl.

As discussed above, the process of the invention may be used to produce PET ligands. In one embodiment, the deprotected product is a PET ligand. As mentioned above, PET ligands are well known to the skilled person. In particular, the deprotected product may be a PET ligand comprising an $^{18}$F atom bonded to an sp$^2$ hybridized carbon atom.

In one embodiment, the deprotected product is a compound of formula (XXIX), (XXX), (XXXI), (XXXII), (XXXIII) or (XXXIV):

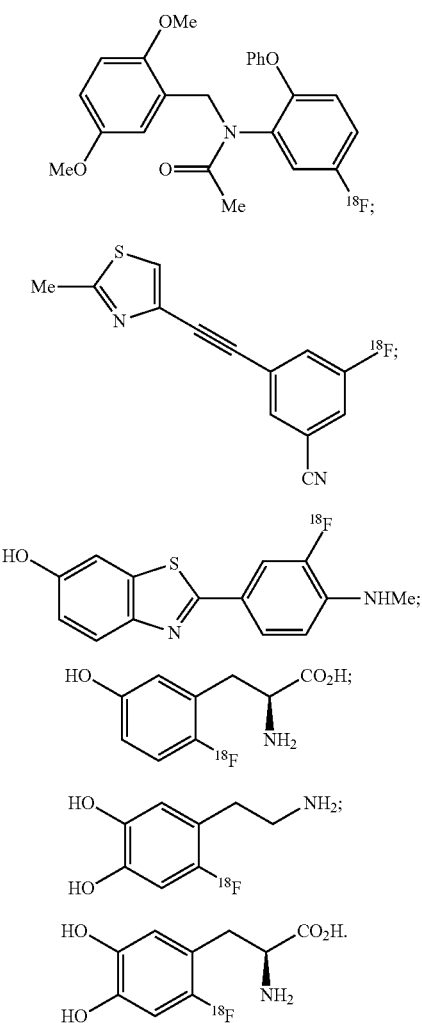

Particular Processes According to the Invention

In one embodiment, the process of the invention is a process for producing a compound of formula (XXXV):

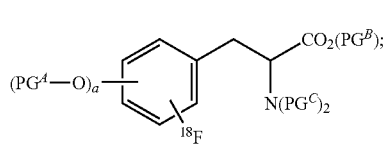

which process comprises treating a compound of formula (XXXVI):

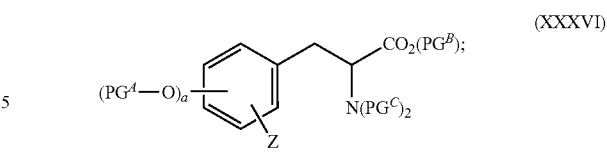

with
$^{18}$F$^-$ and
(ii) a copper compound;
wherein:
each PG$^A$ is independently H or an alcohol protecting group;
PG$^B$ is H or a carboxylic acid protecting group; and
each PG$^C$ is independently H or an amine protecting group;
Z is as defined anywhere hereinbefore; and
a is an integer from 0 to 4.

Often, the process of the invention is a process for producing a compound of formula (XXIV):

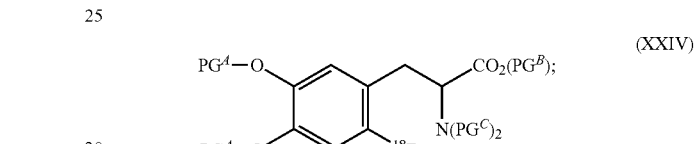

which process comprises treating a compound of formula (XIX):

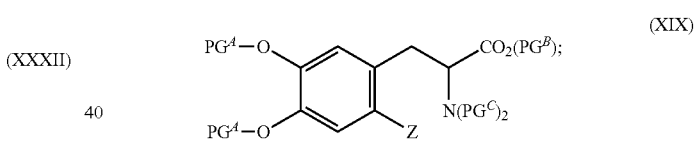

with
(i) $^{18}$F$^-$ and
(ii) a copper compound;
wherein:
each PG$^A$ is independently H or an alcohol protecting group;
PG$^B$ is H or a carboxylic acid protecting group; and
each PG$^C$ is independently H or an amine protecting group; and
Z is as defined anywhere hereinbefore.

For instance, the process of the invention may be a process for producing a compound of formula (XXIV-L):

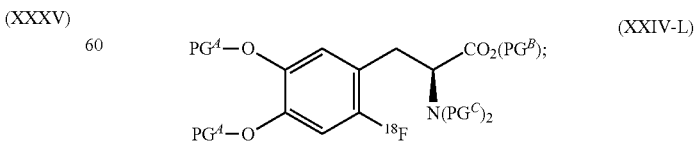

which process comprises treating a compound of formula (XIX-L):

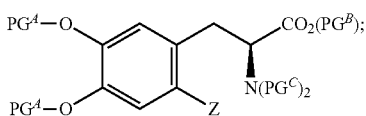
(XIX-L)

with
(i) [¹⁸F]⁻ and
(ii) a copper compound;
wherein:
  each $PG^A$ is independently H or an alcohol protecting group;
  $PG^B$ is H or a carboxylic acid protecting group; and
  each $PG^C$ is independently H or an amine protecting group; and
Z is as defined anywhere hereinbefore.

In one embodiment, the process of the invention is a process for producing a compound of formula (XXV):

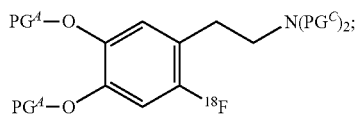
(XXV)

which process comprises treating a compound of formula (XX):

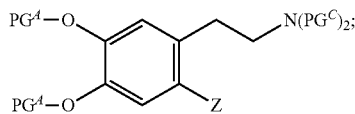
(XX)

with
(i) [¹⁸F]⁻ and
(ii) a copper compound;
wherein:
  each $PG^A$ is independently H or an alcohol protecting group;
  each $PG^C$ is independently H or an amine protecting group; and
Z is as defined anywhere hereinbefore.

In one embodiment, the process of the invention is a process for producing a compound of formula (XXVI):

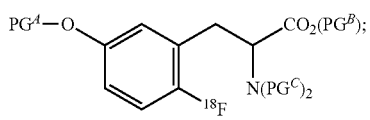
(XXVI)

which process comprises treating a compound of formula (XXI):

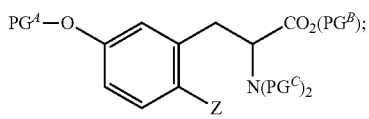
(XXI)

with
(i) [¹⁸F]⁻ and
(ii) a copper compound;
wherein:
  each $PG^A$ is independently H or an alcohol protecting group;
  $PG^B$ is H or a carboxylic acid protecting group; and
  each $PG^C$ is independently H or an amine protecting group; and
Z is as defined anywhere hereinbefore.

For instance, the process of the invention may be a process for producing a compound of formula (XXVI-L):

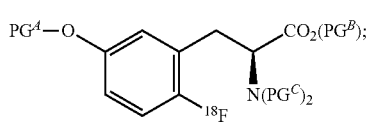
(XXVI-L)

which process comprises treating a compound of formula (XXI-L):

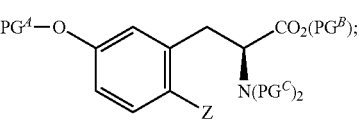
(XXI-L)

with
(i) [¹⁸F]⁻ and
(ii) a copper compound;
wherein:
  each $PG^A$ is independently H or an alcohol protecting group;
  $PG^B$ is H or a carboxylic acid protecting group; and
  each $PG^C$ is independently H or an amine protecting group; and
Z is as defined anywhere hereinbefore.

For each of these processes according to the invention, $PG^A$, $PG^B$ and $PG^C$ may be as described anywhere hereinbefore. For instance: each $PG^A$ may be independently H or an alcohol protecting group selected from substituted or unsubstituted $C_{1-10}$ alkyl, substituted or unsubstituted —C(O)—$C_{1-10}$ alkyl, substituted or unsubstituted —$C_{1-10}$ alkylene-O—$C_{1-10}$ alkyl optionally wherein the $C_{1-10}$ alkylene group and $C_{1-10}$ alkyl group may be bonded together to form a ring, and substituted or unsubstituted tri($C_{1-10}$ alkyl) silyl; $PG^B$ may be H or a carboxylic acid protecting group selected from substituted or unsubstituted $C_{1-10}$ alkyl, substituted or unsubstituted —C(O)—$C_{1-10}$ alkyl, and substituted or unsubstituted tri($C_{1-10}$ alkyl) silyl; and each $PG^C$ may be independently H or an amine protecting group selected from substituted or unsubstituted $C_{1-10}$ alkyl, substituted or unsubstituted —C(O)—$C_{1-10}$ alkyl, substituted or unsubstituted —C(O)—O—$C_{1-10}$ alkyl, substituted or unsubstituted —S(O)₂-aryl.

For instance, each $PG^A$ may be independently H or a group selected methyl, ethyl, tert-butyl, and benzyl; $PG^B$ may be group selected from methyl, ethyl, tert-butyl, and benzyl; and each $PG^C$ may be independently H or a group selected from carbobenzyloxy (Cbz), p-methoxybenzyl carbonyl (Moz), tert-butyloxycarbonyl (Boc), 9-fluorenylmethyloxycarbonyl (FMOC), acetyl, benzoyl, and benzyl.

For each of these processes according to the invention, the copper compound may be as further defined anywhere hereinbefore. The source of $^{18}F^-$ may be as defined anywhere hereinbefore. The process conditions may be as further defined anywhere hereinbefore. As mentioned, Z may be as defined hereinbefore. For instance, Z may be a boronic ester group, for instance a pinacol boronic ester.

For each of these processes according to the invention, the process may further comprises a step of removing one or more protecting groups from the compound comprising an $^{18}F$ atom to produce a deprotected product. The deprotected product is typically a PET ligand, as discussed above. Often, the deprotected product is a compound of formula (XXXII), (XXXIII) or (XXXIV):

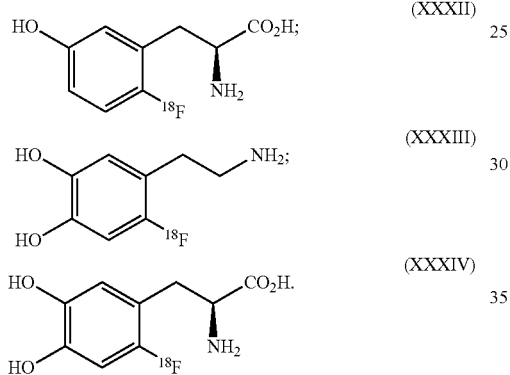

Automated Process

In one embodiment of the invention, the process is conducted in an automated synthesizer. The automated synthesizer may be any suitable automated synthesizer, as are well known to the skilled person. Automated synthesizers may include one or more means for performing the process of the invention. For instance, an automated synthesizer may comprise one or more of (i) a means for mixing the reagents used in the process of the invention, (ii) a means for heating the mixed reagents of the invention and (iii) means for isolating the compound comprising an $^{18}F$ atom. Such automated synthesizers may be used for the production of PET ligands comprising an $^{18}F$ atom. Thus, the automated synthesizer may be suitable for use in a clinical setting, for instance in a imaging centre equipped with PET imaging and/or scanning apparatus.

An automated synthesizer may comprise one or more reagents used in the process of the invention. For example, the automated synthesizer may be pre-loaded with one or more reagents, for instance an organoboron compound as described anywhere herein or a copper compound as described anywhere herein. Alternatively, the process of the invention may be conducted in an automated synthesizer, which process further comprises loading the automated synthesizer with one or more reagents. The reagents may be loaded into the automated synthesizer by inserting a pre-packaged amount of the reagent, for instance in the form of a capsule. For instance, the process of the invention may further comprise (prior to treating the organoboron compound with the copper compound and $^{18}F^-$) inserting a pre-packaged sample of a copper compound as defined anywhere herein or an organoboron compound as defined anywhere herein into an automated synthesizer.

Compounds

The process of the invention allows the production of radiolabelled compounds. The inventors have found that certain organoboron compounds are particularly well suited to use in the process of the invention. In particular, compounds having a doubly protected amine group are useful because the presence of two protecting groups on the amine prevents side reactions which may cause ring closure between the amine group and an aryl ring in the organoboron compound.

Thus, the invention also provides a compound of formula (XXXVII):

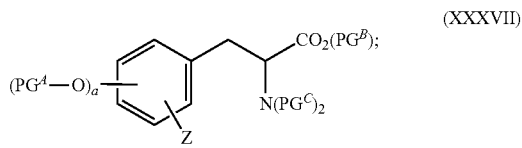

wherein:
each $PG^A$ is independently H or an alcohol protecting group;
$PG^B$ is H or a carboxylic acid protecting group;
each $PG^C$ is independently an amine protecting group;
Z is a group selected from a boronic ester group, a boronic acid group, a borate group, and a trifluoroborate group; and
a is an integer from 0 to 4.

$PG^A$, $PG^B$, $PG^C$, Z and a may be as defined anywhere hereinbefore.

In particular, each $PG^A$ may be independently H or an alcohol protecting group selected from substituted or unsubstituted $C_{1-10}$ alkyl, substituted or unsubstituted —C(O)—$C_{1-10}$ alkyl, substituted or unsubstituted —$C_{1-10}$ alkylene-O—$C_{1-10}$ alkyl optionally wherein the $C_{1-10}$ alkylene group and $C_{1-10}$ alkyl group may be bonded together to form a ring, and substituted or unsubstituted tri($C_{1-10}$ alkyl) silyl; $PG^B$ may be H or a carboxylic acid protecting group selected from substituted or unsubstituted $C_{1-10}$ alkyl, substituted or unsubstituted —C(O)—$C_{1-10}$ alkyl, and substituted or unsubstituted tri($C_{1-10}$ alkyl) silyl; each $PG^C$ may be independently an amine protecting group selected from substituted or unsubstituted $C_{1-10}$ alkyl, substituted or unsubstituted —C(O)—$C_{1-10}$ alkyl, substituted or unsubstituted —C(O)—O—$C_{1-10}$ alkyl, substituted or unsubstituted —S(O)$_2$-aryl; Z is a group selected from a boronic ester group, a boronic acid group, a borate group, and a trifluoroborate group; and a is an integer from 0 to 4.

In one embodiment of the compound of the invention, each $PG^A$ is independently H or an alcohol protecting group selected from $C_{1-10}$ alkyl optionally substituted with one or more unsubstituted aryl groups, —C(O)—$C_{1-10}$ alkyl optionally substituted with one or more unsubstituted aryl groups, —$C_{1-10}$ alkylene-O—$C_{1-10}$ alkyl optionally substituted with one or more unsubstituted aryl groups and optionally wherein the $C_{1-10}$ alkylene group and $C_{1-10}$ alkyl group may be bonded together to form a ring, and tri($C_{1-10}$ alkyl) silyl optionally substituted with one or more unsubstituted aryl groups; $PG^B$ is H or a carboxylic acid protecting group selected from $C_{1-10}$ alkyl optionally substituted with one or more unsubstituted aryl groups, and tri($C_{1-10}$ alkyl) silyl optionally substituted with one or more unsubstituted aryl groups; and each $PG^C$ is independently an amine protecting group selected from $C_{1-10}$ alkyl optionally substituted with one or more unsubstituted aryl groups, —C(O)—$C_{1-10}$ alkyl optionally substituted with one or more unsubstituted aryl groups, and —C(O)—O—$C_{1-10}$ alkyl optionally substituted with one or more unsubstituted aryl groups; Z is a group selected from a boronic ester group, a boronic acid group, a borate group, and a trifluoroborate group; and a is an integer from 0 to 4.

For instance: each $PG^A$ may be independently H or a group selected methyl, ethyl, tert-butyl, benzyl, p-methoxybenzyl, trityl, acetyl, benzoyl, pivaloyl, methoxymethyl, methoxyethoxymethyl, methoxytrityl, dimethoxytrityl, tetrahydrofuranyl, tetrahydropyranyl, trimethylsilyl, tert-butyldimethylsilyl, tri-iso-propyl silyloxymethyl, and tri-iso-propylsilyl; $PG^B$ may be H or a group selected from methyl, ethyl, tert-butyl, benzyl, p-methoxybenzyl, trityl, trimethylsilyl, tert-butyldimethylsilyl, tri-iso-propyl silyloxymethyl, and tri-iso-propylsilyl; and each $PG^C$ may be independently a group selected from carbobenzyloxy (Cbz), p-methoxybenzyl carbonyl (Moz), tert-butyloxycarbonyl (Boc), 9-fluorenylmethyloxycarbonyl (FMOC), acetyl, benzoyl, benzyl, p-methoxybenzyl (PMB), 3,4-dimethoxylbenzyl (DMPM), p-methoxyphenyl (PMP), tosyl (Ts) and Nosyl.

In a preferred embodiment, each $PG^A$ is independently H or a group selected from methyl, ethyl and benzyl; $PG^B$ is H or a group selected from methyl, ethyl, tert-butyl, or benzyl; and each $PG^C$ is independently a group selected from carbobenzyloxy (Cbz), p-methoxybenzyl carbonyl (Moz), tert-butyloxycarbonyl (Boc), 9-fluorenylmethyloxycarbonyl (FMOC), acetyl, and benzoyl.

For instance, $PG^C$ is often tert-butyloxycarbonyl (Boc).

Z may be as further defined anywhere hereinbefore. For instance, Z may be a boronic ester group such as those of formula (V), (VI) or (VII) above. Z may be a pinacol boronic ester.

In one embodiment, a is 1 or 2.

The compound of the invention may be a compound of formula (XXXVIII) or (XXXIX):

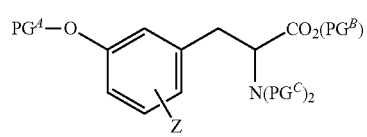
(XXXVIII)

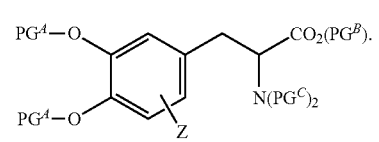
(XXXIX)

The compound may be a compound of formula (XL) or (XLI):

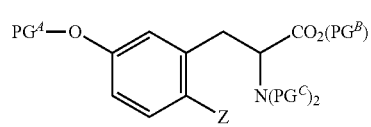
(XL)

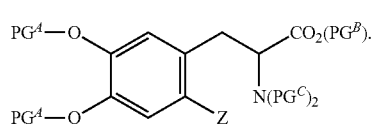
(XLI)

The compound may be a compound of formula (XLII) or (XLIII):

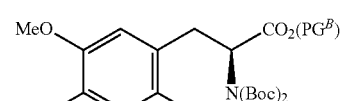
(XXVIII)

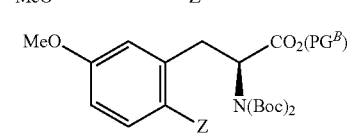
(XLIII)

The compound may be a compound of formula (XLIV), (XLV), (XLVI) or (XLVII):

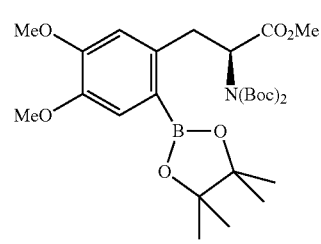
(XLIV)

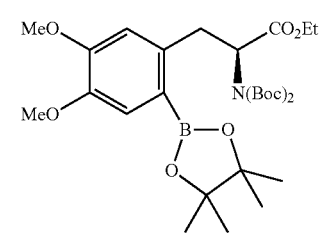
(XLV)

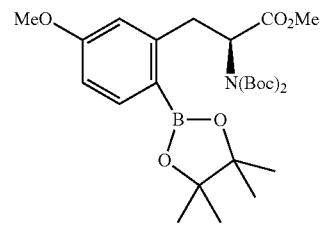
(LXVI)

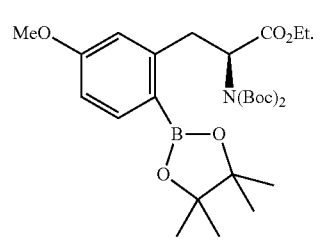
(LXVII)

The compound may be a compound of formula (XLIV) or (XLV):

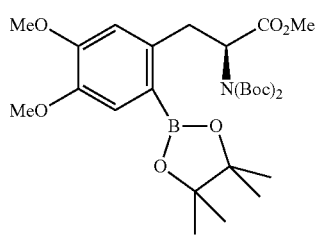

(XLIV)

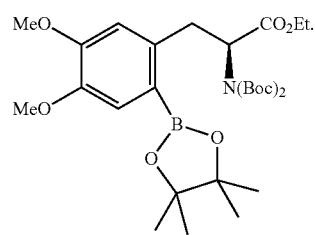

(XLV)

Use of an Organoboron Compound

The invention also provides the use of an organoboron compound, which organoboron compound comprises a boron atom bonded to an sp² hybridised carbon atom, in a process for producing an organic compound comprising an $^{18}$F atom, which process comprises treating said organoboron compound with (i) $^{18}$F⁻ and
(ii) a copper compound.

In the use according to the invention, the process for producing an organic compound comprising an $^{18}$F atom may be as further defined anywhere hereinbefore.

The organoboron compound may be as described anywhere hereinbefore. For instance, the organoboron compound may be an organoboron compound as defined in any one of formulae (II), (III), (VIII), (IX), (X), (XI), (XII), (XIII), (XIV), (XV), (XVI), (XVII), (XVIII), (XIX), (XX), (XXI), (XXII) or (XXIII).

The invention is further described in the following Examples.

EXAMPLES

Materials and Methods

1. General Experimental Information

All NMR spectra were recorded on Bruker DPX200, DPX250, AV400, AVC500, AVB500 and DRX500 spectrometers. Proton and carbon-13 NMR spectra are reported as chemical shifts (δ) in parts per million (ppm) relative to the solvent peak using the Bruker internal referencing procedure (edlock). Fluorine-19 NMR spectra are referenced relative to CFCl₃ in CDCl₃. Coupling constants (J) are reported in units of hertz (Hz). The following abbreviations are used to describe multiplicities—s (singlet), d (doublet), t (triplet), q (quartet), m (multiplet) brs (broad singlet). High resolution mass spectra (HRMS, m/z) were recorded on a Bruker MicroTOF spectrometer using positive electrospray ionization (ESI⁺) or on a Micromass GCT spectrometer using filed ionization (Fr) or chemical ionization (CI⁺). Infrared spectra were recorded either as the neat compound or in a solution using a Bruker Tensor 27 FT-IR spectrometer. Absorptions are reported in wavenumbers (cm⁻¹) and only peaks of interest are reported. Optical rotations were measured on a PerkinElmer Polarimeter model 341 Specific rotations are reported in 10⁻¹ deg cm² g⁻¹ and concentrations in g/100 mL. Melting points of solids were measured on a Griffin apparatus and are uncorrected. IUPAC names were obtained using the ACD/I-Lab service. Solvents were purchased from Fisher, Rathburn or Sigma-Aldrich. When dry solvents were required they were purified by expression through an activated alumina column built. Chemicals were purchased from Acros, Alfa Aesar, Fisher, Fluorochem, Sigma-Aldrich and used as received. Reactions were monitored by thin-layer chromatography (TLC) carried out on Merck Kiesegel 60 F254 plates, silica gel column chromatography was performed over Merck silica gel C60 (40-60 μm).

2. Experimental Procedures and Characterisation Data (Hetero)aryl pinacol boronate esters were purchased from commercial sources, or synthesised based on known procedures.

Ethyl 2-((tert-butoxycarbonyl)amino)-3-(2-4,4,5,5-tetramethyl-1,3,2-dioxaborolan-2-yl-4,5-dimethoxyphenyl)propanoate

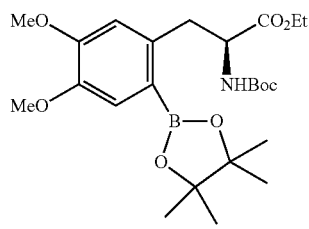

Bis(pinacolato)diboron (698 mg, 2.75 mmol), Pd(dppf) Cl₂·CH₂Cl₂ (102 mg, 0.125 mmol) and potassium acetate (736 mg, 7.5 mmol) were placed in a dry place under N₂. DMF (15 mL) was added and the mixture purged with N₂ for 15 minutes. Ethyl (S)-2-((tert-butoxycarbonyl)amino)-3-(2-iodo-4,5-dimethoxyphenyl)propanoate (1.20 g, 2.5 mmol) was added and the mixture was heated to 80° C. and stirred at this temperature for 18 hours. The reaction mixture was allowed to cool to room temperature and brine (20 mL) was added, followed by extraction with Et₂O (3×20 mL). The combined organic extracts were washed with brine (30 mL), dried (MgSO₄), filtered and concentrated in vacuo. Flash column chromatography (10-25% EtOAc in hexane afforded the title compound as a white solid (740 mg, 62%). TLC (33% EtOAc in hexane) R$_f$=0.41. Two rotamers present at 25° C. in an 81:19 ratio. ¹H NMR (400 MHz, CD₂Cl₂) δ 7.25 (s, 1H), 6.75 (s, 1H), 5.94 (d, J=7.9 Hz, 0.81H), 5.37 (br s, overlaps with solvent peak), 4.28-4.15 (m, 3H), 3.85 (s, 3H), 3.84 (s, 3H), 3.24-3.13 (m, 2H), 1.38 (s, 6H), 1.37 (s, 6H), 1.34-1.23 (overlapping peaks, 12H); ¹³C NMR (100 MHz, CD₂Cl₂) δ 172.7, 155.5, 151.6, 147.3, 137.9, 118.2, 113.2, 84.0, 78.9, 60.9, 56.5, 55.8, 55.6, 36.6, 28.0, 24.8, 24.4, 14.0; ¹¹B NMR (128 MHz, CD₂Cl₂) δ 31 (br s).

Ethyl 2-((di-tert-butoxycarbonyl)amino)-3-(2-4,4,5,5-tetramethyl-1,3,2-dioxaborolan-2-yl-4,5-dimethoxyphenyl)propanoate

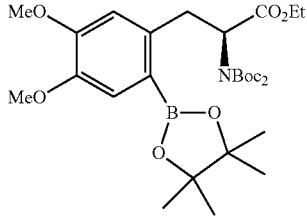

To a solution of Ethyl (S)-2-((tert-butoxycarbonyl)amino)-3-(4,5-dimethoxy-2-(4,4,5,5-tetramethyl-1,3,2-dioxaborolan-2-yl)phenyl)propanoate (240 mg, 0.5 mmol, 1 eq.) in MeCN (2 mL) was added di-tert-butyl dicarbonate (328 mg, 1.5 mmol, 3 eq.), N,N-dimethylaminopyridine (12 mg, 0.1 mmol, 0.2 eq.) and Et$_3$N (210 μL, 1.5 mmol, 3 eq.). The mixture was stirred at room temperature under N$_2$ for 18 hours. The solvent was removed in vacuo. The residue was dissolved in EtOAc (5 mL) and washed with NH$_4$Cl (sat. aq. Solution, 5 mL), water (5 mL) and brine (5 mL). The organic extract was dried (MgSO$_4$), filtered and concentrated in vacuo. Flash column chromatography (15-25%) EtOAc in hexane afforded impure title compound (189 mg). This was purified by preparative HPLC to afford the title compound (153 mg, 53%). TLC (33% EtOAc in hexane) R$_f$=0.54. $^1$H NMR (400 MHz, CD$_2$Cl$_2$) δ 7.22 (s, 1H), 6.56 (s, 1H), 5.18 (dd, J=11.2, 3.9 Hz, 1H), 4.21 (m, 2H), 3.95 (dd, J=13.4, 3.9, 1H), 3.81 (s, 3H), 3.80 (s, 3H), 3.05 (dd, J=13.4, 11.4, 1H) 1.33 (s, 24H), 1.31 (s, 6H), 1.28 (t, J=7.2 Hz, 3H); $^{13}$C NMR (100 MHz, CD$_2$Cl$_2$) δ 170.9, 152.7, 151.6, 147.6, 139.3, 119.3, 115.0, 84.0, 82.8, 61.6, 60.9, 56.5, 56.0, 35.6, 28.2, 25.2, 14.7; $^{11}$B NMR (128 MHz, CD$_2$Cl$_2$) δ 31 (br s).

Methyl (Z)-2-((tert-butoxycarboyl)amino)-3-(2-fluoro-5-methoxyphenyl)acrylate

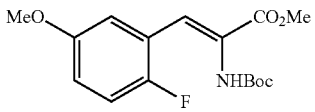 [SMILES: COC(=O)/C(=C/c1cc(OC)ccc1F)NC(=O)OC(C)(C)C]

($^1$H NMR, 400 MHz, CDCl$_3$): δ=7.21 (s, 1H), 7.02-7.06 (m, 1H), 6.91 (t, J=10 Hz, 1H), 6.73-6.78 (m, 1H), 6.36 (bs, 1H), 3.79 (s, 3H), 3.68 (s, 3H), 1.31 (br s, 9H); ($^{13}$C NMR, 100 MHz, CDCl$_3$): δ=165.6, 155.3, 155.1 (d, J=244 Hz), 152.4, 126.3, 122.7 (d, J=15 Hz), 120.9 (d, J=4 Hz), 116.4 (d, J=8 Hz), 116.2 (d, J=24 Hz), 113.6 (d, J=2 Hz), 81.1, 55.7, 52.7, 28.0; ($^{19}$F NMR, 377 MHz, CDCl$_3$): δ=−123.1 (br s); IR: ν 2979, 1709, 1494, 1368, 1245, 1210 cm$^{-1}$; FIRMS (ESI) for C$_{16}$H$_{20}$FNNaO$_5$ [M+Na]$^+$ requires 348.1218 found 348.1219.

Methyl (Z)-2-((tert-butoxycarbonyl)amino)-3-(2-fluoro-4,5-dimethoxyphenyl)acrylate

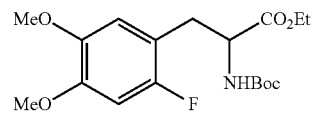 [SMILES: CCOC(=O)C(Cc1cc(OC)c(OC)cc1F)NC(=O)OC(C)(C)C]

($^1$H NMR, 400 MHz, CDCl$_3$): δ=7.39 (s, 1H), 7.19 (d, J=7 Hz, 1H), 6.61 (d, J=12 Hz, 1H), 3.87 (s, 3H), 3.84 (s, 3H), 3.82 (s, 3H) 1.33 (bs, 9H); ($^{13}$C NMR, 100 MHz, CDCl$_3$): δ=165.9, 155.8 (d, J=246 Hz), 152.8, 151.0 (d, J=10 Hz), 145.0 (d, J=2 Hz), 123.9, 122.2 (d, J=4 Hz), 113.2 (d, J=13 Hz), 110.7 (d, J=3 Hz), 99.6 (d, J=28 Hz), 80.9, 56.2, 56.1, 52.6, 28.1; ($^{19}$F NMR, 377 MHz, CDCl$_3$): δ=−118.9 (broad singlet); IR: ν 3332, 2977, 1716, 1515, 1258 cm$^{-1}$; HRMS (ESI) for C$_{17}$H$_{22}$FNNaO$_6$ [M+Na]$^+$ requires 378.1323 found 378.1323.

Ethyl 2-((tert-butoxycarbonyl)amino)-3-(2-fluoro-4,5-dimethoxyphenyl)propanoate

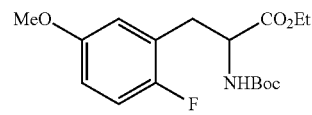

Two rotamers present at 25° C. in an 85:15 ratio. ($^1$H NMR, 400 MHz, CDCl$_3$): δ=6.51-6.56 (m, 2H), 5.02 (d, J=8 Hz, 0.88H), 4.69-4.86 (bs, 0.14H, rotamer), 4.41-4.48 (m, 0.89H), 4.22-4.32 (bs, 0.16H, rotamer), 4.06-4.14 (m, 2H), 3.77 (s, 3H), 3.76 (s, 3H), 2.81-3.07 (m, 2H, +rotamer), 1.34 (s, 9H), 1.18 (t, J=7 Hz, 3H); ($^{13}$C NMR, 100 MHz, CDCl$_3$): δ=171.8, 155.4 (d, J=232 Hz), 155.0, 148.8 (d, J=15 Hz), 145.1, 113.5 (d, J=3 Hz), 113.4 (d, J=20 Hz), 99.9 (d, J=29 Hz), 79.8, 61.4, 56.3, 56.1, 53.8, 31.4, 28.3, 14.1; ($^{19}$F NMR, 377 MHz, CDCl$_3$): δ=−124.8; IR: ν 2978, 1713, 1626, 1516, 1226, 1193 cm$^{-1}$; HRMS (ESI) for C$_{18}$H$_{26}$FNNaO$_6$ [M+Na]$^+$ requires 394.1636 found 394.1640.

Ethyl 2-((tert-butoxycarbonyl)amino)-3-(2-fluoro-5-methoxyphenyl)propanoate

Two rotamers present at 25° C. in an 83:17 ratio. ($^1$H NMR, 400 MHz, CDCl$_3$): δ=6.92 (t, J=9 Hz, 1H), 6.62-6.74 (m, 2H), 5.08 (bd, J=8 Hz, 0.81H), 4.78-4.90 (bs, 0.18H, rotamer), 4.49-4.57 (m, 0.82H), 4.30-4.43 (bs, 0.18H, rotamer), 4.12-4.19 (m, 2H), 3.74 (s, 3H), 2.84-3.16 (m, 2H, +rotamer), 1.39 (s, 9H), 1.22 (t, J=7 Hz, 3H); ($^{13}$C NMR, 100 MHz, CDCl$_3$): δ=171.7, 155.8 (d, J=238 Hz), 155.5, 155.0, 123.9 (d, J=18 Hz), 116.4 (d, J=4 Hz), 115.7

(d, J=24 Hz), 113.6 (d, J=8 Hz), 79.8, 61.5, 55.7, 53.7, 32.1, 28.3, 14.0; ($^{19}$F NMR, 377 MHz, CDCl$_3$): δ=−128.3; IR: ν 2979, 1713, 1500, 1367, 1251, 1210, 1163 cm$^{-1}$; HRMS (ESI) for C$_{17}$H$_{24}$FNNaO$_5$ [M+Na]$^+$ requires 364.1531 found 364.1541.

(E)-4,4,5,5-tetramethyl-2-(4-styrylphenyl)-1,3,2-dioxaborolane

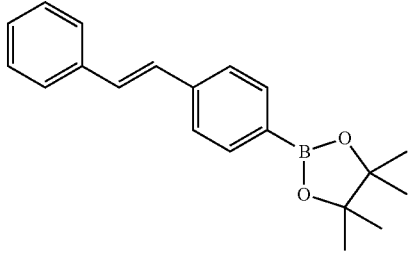 [SMILES: CC1(C)OB(c2ccc(/C=C/c3ccccc3)cc2)OC1(C)C]

Pd(dppf)Cl$_2$·CH$_2$Cl$_2$ (141.0 mg, 0.2 mmol) was added to a mixture of (E)-1-bromo-4-styrylbenzene (1.0 g, 3.9 mmol), potassium acetate (1.1 g, 11.6 mmol) and 4,4,4',4',5,5,5',5'-octamethyl-2,2'-bi(1,3,2-dioxaborolane) (1.0 g, 4.1 mmol) in DMF (3 mL). The mixture was stirred at 130° C. under nitrogen for 16 hours. The insoluble solid was removed by filtration through Celite pad (eluted with EtOAc) and diluted with H$_2$O (30 mL) and extracted with EtOAc (3×30 mL). The combined organic extracts were washed with brine (30 mL), dried over MgSO$_4$ and concentrated in vacuum to give the crude product. The residue was dissolve in EtOAc (30 mL) and then activated-carbon powder and silica-gel were added and the mixture was shaken, sonicated and filtered through silica-gel/Celite pad (eluted with EtOAc). The filtrate was concentrated in vacuum and the residue was further purified by crystallization from hot hexane and dried under vacuum to yield a white solid (818 mg, 69%).

($^1$H NMR, 400 MHz, CDCl$_3$): δ=7.84 (d, J=8.0 Hz, 2H), 7.56-7.54 (d, J=8.0 Hz, 4H), 7.38 (t, J=7.5 Hz, 2H), 7.29 (d, J=7.5 Hz, 1H), 7.21 (d, J=16.3 Hz, 1H), 7.14 (d, J=16.3 Hz, 1H), 1.38 (s, 12H); ($^{13}$C NMR, 100 MHz, CDCl$_3$): δ=140.1, 137.3, 135.3, 129.8, 128.8, 128.7, 127.9, 126.7, 125.9, 83.8, 25.0.

1-Chloro-4-(trimethylsilyl)but-3-yn-2-one

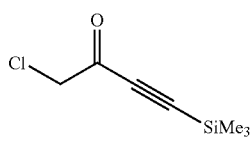

($^1$H NMR, 400 MHz, CDCl$_3$): δ=4.23 (s, 2H), 0.26 (s, 9H); 7.48 (t, J=7.2 Hz, 2H), 7.41 (t, J=7.2 Hz, 1H), 7.36 (d, J=8.8 Hz, 2H); bp 80° C. (14 mbar).

2-Methyl-4-((trimethylsilyl)ethynyl)thiazole

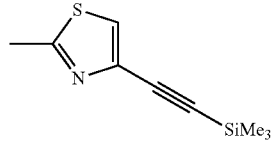

($^1$H NMR, 400 MHz, CDCl$_3$): δ=7.30 (s, 1H), 2.67 (s, 3H), 0.22 (s, 9H); ($^{13}$C NMR, 100 MHz, CDCl$_3$): δ=165.6, 137.0, 123.0, 98.4, 94.6, 19.3, −0.1.

3-Bromo-5-((2-methylthiazol-4-yl)ethynyl)benzonitrile

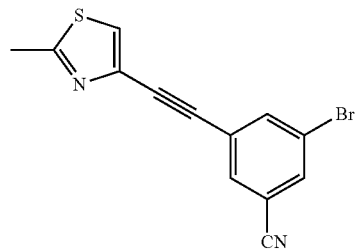 [SMILES: Cc1nc(C#Cc2cc(Br)cc(C#N)c2)cs1]

($^1$H NMR, 400 MHz, CDCl$_3$): δ=7.89 (s, 1H), 7.74-7.72 (m, 2H), 7.45 (s, 1H), 2.74 (s, 3H); ($^{13}$C NMR, 100 MHz, CDCl$_3$): δ=166.4, 138.6, 135.7, 134.4, 133.5, 126.0, 124.2, 122.9, 116.7, 114.5, 87.3, 85.1, 19.4.

3-((2-Methylthiazol-4-yl)ethynyl)-5-(4,4,5,5-tetramethyl-1,3,2-dioxaborolan-2-yl)benzonitrile

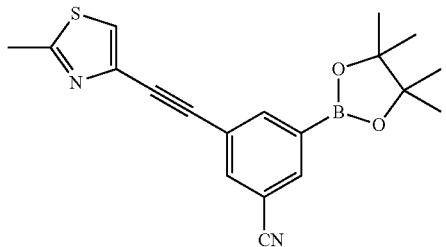

Nitrogen was bubbled through a mixture of 3-bromo-5-[(2-methyl-1,3-thiazol-4-yl)ethynyl]benzonitrile (440.0 mg, 1.45 mmol), bis(pinacolato)diboron (405 mg, 1.60 mmol), potassium acetate (570 mg, 5.80 mmol), dichloro[1,1'-bis(diphenylphosphino)ferrocene]-palladium(II) dichloromethane adduct (71 mg, 0.09 mmol) and N,N-dimethylacetamide (4.5 mL) for 1 h. Then the reaction was heated at 110° C. for 20 min, cooled to room temperature and diluted with H$_2$O (50 mL), and extracted with EtOAc (4×30 mL). The combined organic extracts were washed with brine (30 mL), dried (MgSO$_4$), filtered, and concentrated in vacuum to give a residue that was dissolve in Et$_2$O/hexane (5/1) and filtered through a small silica-gel column. The filtrate was concentrated in vacuum and the residue was purified by crystallization from hot acetonitrile (placed in the freezer) to afford the crude product that was washed several times with n-dibutyl ether to yield a white solid (139 mg, 27%).

($^1$H NMR, 400 MHz, CD$_2$Cl$_2$): δ=8.16 (s, 1H), 8.01 (s, 1H), 7.86 (s, 1H), 7.46 (s, 1H), 2.71 (s, 3H), 1.35 (s, 12H); $^{13}$C NMR (101 MHz, CD$_2$Cl$_2$) δ 166.4, 142.1, 138.1, 137.1, 136.5, 124.1, 123.9, 118.4, 113.0, 86.4, 86.2, 85.2, 25.1, 19.4; IR: ν 2979, 2232, 1589, 1412, 1371, 1329, 1242, 1143, cm$^{-1}$.

3. Radiochemistry

[$^{18}$F]Fluoride was produced by PETNet Solutions at Mount Veron Hospital (UK) via the $^{18}$O (p,n)$^{18}$F reaction and delivered as [$^{18}$F]fluoride in [$^{18}$O]water. Radiosynthesis and azeotropic drying was performed on a NanoTek® automated microfluidic device (Advion). [$^{18}$F]Fluoride was separated from $^{18}$O-enriched-water using anion exchange cartridges (MP1, ORTG, Tennessee, USA or $^{18}$F separation cartridges, 45 mg) and subsequently released with by 550 μL of a solution of K$_{222}$/K$_2$CO$_3$ (kryptofix 222 (15 mg) and K$_2$CO$_3$ (3 mg) in 1 mL of MeCN/H$_2$O, 4:1) into the concentrator. Alternatively [$^{18}$F]Et$_4$NF was prepared by releasing with 550 μL of a solution of Et$_4$NHCO$_3$ (7 mg in 1 mL of MeCN/H$_2$O, 4:1). The solution was dried with five cycles of azeotropic drying with acetonitrile (300 μl) and redissolved in anhydrous acetonitrile (500-1000 μL). HPLC analysis was performed with a Dionex Ultimate 3000 dual channel HPLC system equipped with shared autosampler, parallel UV-detectors and LabLogic NaI/PMT-radiodetectors with Flowram analog output. Radio-TLC was performed on Merck Kieselgel 60 F254 plates. Analysis was performed using a plastic scintillator/PMT detector.

All radiochemical yields quoted are decay corrected. Radiochemical yields are calculated by radioTLC, taking into account the radiochemical purity observed by radio-HPLC.

4. General Procedure for [$^{18}$F]Fluorination

To a V-vial containing (Pyr)$_4$Cu(OTf)$_2$ (3.6 mg, 0.0053 mmol), (hetero)aryl pinacol boronate (0.06 mmol) and a magnetic stirrer bar was added [$^{18}$F]KF/K$_{222}$ in MeCN. DMF (300 μL) was added via syringe. The sealed vial was heated at 110° C. for 20 minutes. The reaction was quenched by addition of water (200 μL). An aliquot was removed for analysis by radioTLC and HPLC for radiochemical yield and product identity. Analysis was performed using Gradient A with a Waters Nova-Pak C18 column (4 3.9×150 mm) at a flow rate 1 ml/min.

Example 1—[$^{18}$F]4-fluoro-1,1'-biphenyl

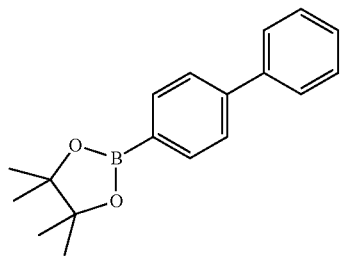

1a

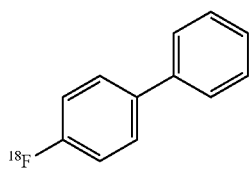

2a 2-([1,1'-Biphenyl]-4-yl)-4,4,5,5-tetramethyl-1,3,2-dioxaborolane 1a served as model substrate for validation and optimization studies. All reactions were conducted without deliberate addition of [$^{19}$F]fluoride (no carrier added). Key parameters were explored to induce [$^{18}$F]incorporation. [$^{18}$F]Fluorination of 1a was observed at 150° C. using [$^{18}$F]KF/K$_{222}$ in dimethylformamide (DMF) or in N-methylpyrrolidone affording [$^{18}$F]4-fluoro-1,1'-biphenyl 2a in low radiochemical yield (RCY~5%); higher RCYs averaging 15% were obtained in DMF at 110° C. It became quickly apparent that the RCYs were affected by the ratio of 1a:Cu (OTf)$_2$. The best results were surprisingly obtained by reducing the amount of Cu complex relative to 1a (ratio 1a:Cu(OTf)$_2$=10:1). The formation of 1,1'-biphenyl and [1,1'-biphenyl]-4-ol resulting from competitive protodeboronation and oxidation respectively were observed. These products are not [$^{18}$F]labeled contaminants but the similar polarities of 1,1'-biphenyl and [$^{18}$F]4-fluoro-1,1'-biphenyl cause complications with purification, so minimizing protodeboronation was an important goal. It was noted that both [$^{18}$F]fluorination and protodeboronation were affected by the protocol applied to evaporate the solution of [$^{18}$F]KF/K$_{222}$ in acetonitrile. Evaporation under N$_2$ led to decreased RCYs and encouraged the formation of 1,1'-biphenyl, an observation indicating that the presence of O$_2$ may be in some instances beneficial for the reaction. These modifications led to the formation of 2a in up to 43% ([1a] 0.26M in DMF). The inventors then focused on the nature of the copper complex itself and the effect of any ligand on reaction efficiency. The experiments encouraged the use of the pyridine copper complex [(Py)$_4$Cu(OTf)$_2$] for selected catalytic transformations. Surprisingly, this complex proved optimal as it afforded 2a in 73% RCY. It is noteworthy that when samples of [(Py)$_4$Cu(OTf)$_2$] and Cu(OTf)$_2$ were left open to air for two weeks, and then employed for radiofluorinations no adverse effect on RCY was observed. The screening of various additives did not significantly improve further the RCY, so the reaction requires only the copper complex, in addition to the substrate and [$^{18}$F]fluoride source. A protocol of the invention therefore started with the preparation of a V-vial containing a magnetic stirrer, [(Py)$_4$Cu(OTf)$_2$] (0.0053 mmol) and ArBPin (0.06 mmol) followed by addition of [$^{18}$F]KF/K222 in MeCN (~30 μL). DMF (300 μL) was added via syringe and the sealed vial heated at 110° C. and allowed to stir for 20 minutes. The reaction was quenched by addition of water (200 μL). An aliquot was removed for analysis by radioactive thin-layer chromatography (radioTLC) and radioactive high-performance liquid chromatography (HPLC) to identify the RCY and derive the product identity, respectively. Analysis was performed using Gradient A with a Waters Nova-Pak C18 column (4 μm, 3.9×150 mm) at a flow rate 1 ml/min. Applying these conditions, [$^{18}$F]4-fluoro-1,1'-biphenyl was obtained in 74% RCY (n=4).

The results of a concentration screen carried out for the biphenyl $^{18}$F fluorination are shown in Table 1 below.

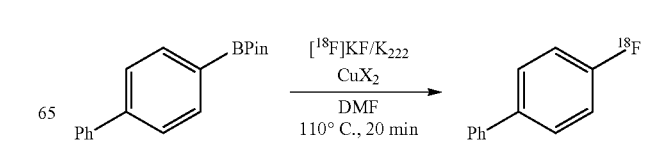

TABLE 1 results of concentration screen.

| entry | [ArBPin] | [Cu] | ArBPin:Cu | RCY (%) |
|---|---|---|---|---|
| 1 | 0.026M | 0.1M | 1:4 | 10 |
| 2 | 0.13M | 0.043 | 3:1 | 31 |
| 3 | 0.13M | 0.026 | 5:1 | 36 |
| 4 | 0.13M | 0.018 | 7:1 | 34 |
| 5 | 0.13M | 0.013 | 10:1 | 35 |
| 6 | 0.13M | 0.0037 | 35:1 | 26 |

Example 2—Presence of Other Functional Groups

To evaluate the utility of the Cu-mediated [$^{18}$F]fluorination, a series of pinacol-derived (hetero)aryl boronic esters was tested. As illustrated in Table 2 below, it was found that numerous functional groups such as alkyl, aryl, aldehyde, ketone, nitro, cyano, amides, ether, ester, alkene, alkyne, morpholino, protected amine and protected alcohol are compatible with this new [$^{18}$F]fluorination with RCY of up to 83%. The following general protocol was used:

To a V-vial containing (Pyr)$_4$Cu(OTf)$_2$ (3.6 mg, 0.0053 mmol), (hetero)aryl pinacol boronate (0.06 mmol) and a magnetic stirrer bar was added [$^{18}$F]KF/K$_{222}$ in MeCN. DMF (300 µL) was added via syringe. The sealed vial was heated at 110° C. for 20 minutes. The reaction was quenched by addition of water (200 µL). An aliquot was removed for analysis by radioTLC and HPLC for radiochemical yield and product identity. Analysis was performed using Gradient A with a Waters Nova-Pak C18 column (4 µm, 3.9×150 mm) at a flow rate 1 ml/min.

Bromo-substituted arylBpin are also suitable substrates, but precursors presenting with unprotected alcohol, amine or sulfonamide functionalities gave lower amounts of the desired [$^{18}$F]product. The reaction of arylBpin with meta-positioned electron withdrawing groups proceeded efficiently, and the presence of electron donating group onto the arylBpin precursor is very well tolerated. Moreover, various ortho-substituted [$^{18}$F]fluoroarenes are also within reach applying the standard protocol. Notably, the reaction can be extended to alkenylBpin precursor as demonstrated with the successful preparation of the [$^{18}$F]fluoroalkene derived from (E)-4,4,5,5-tetramethyl-2-styryl-1,3,2-dioxaborolane. Next, attention was turned to heteroarenes with the knowledge that there is an unmet need for nucleophilic [$^{18}$F]fluorination to access some of these valuable pharmacophores. The [$^{18}$F] labeled 6-fluoroquinoline was obtained in 50% RCY.

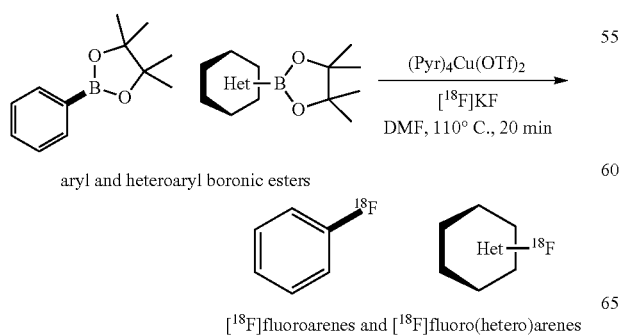

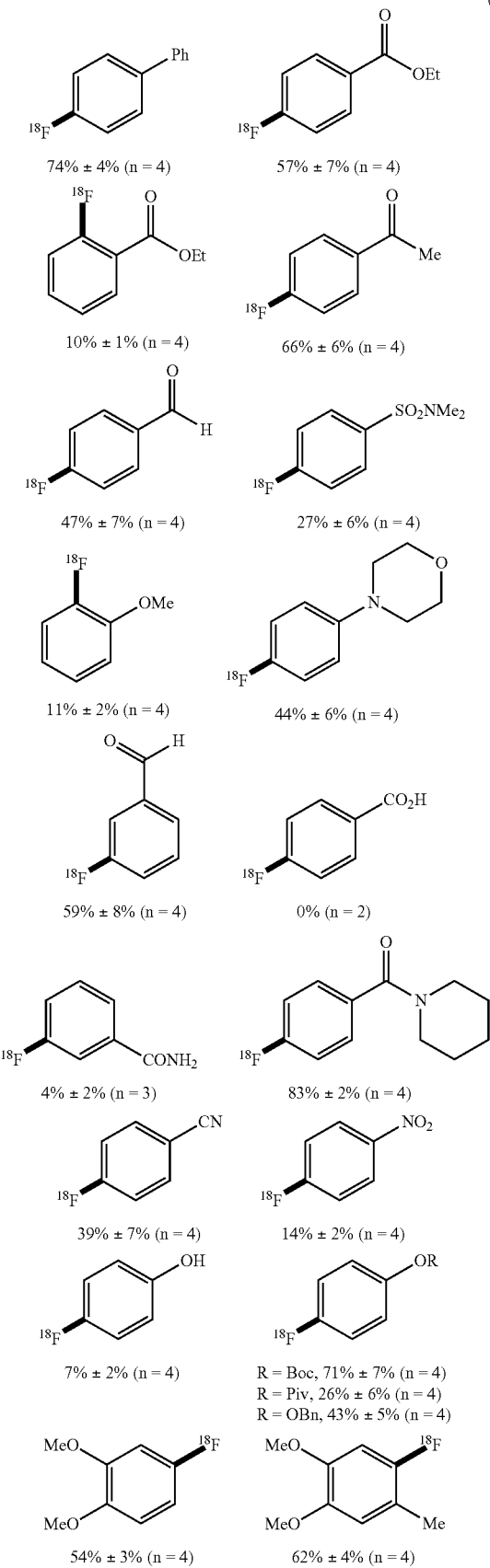

(A)

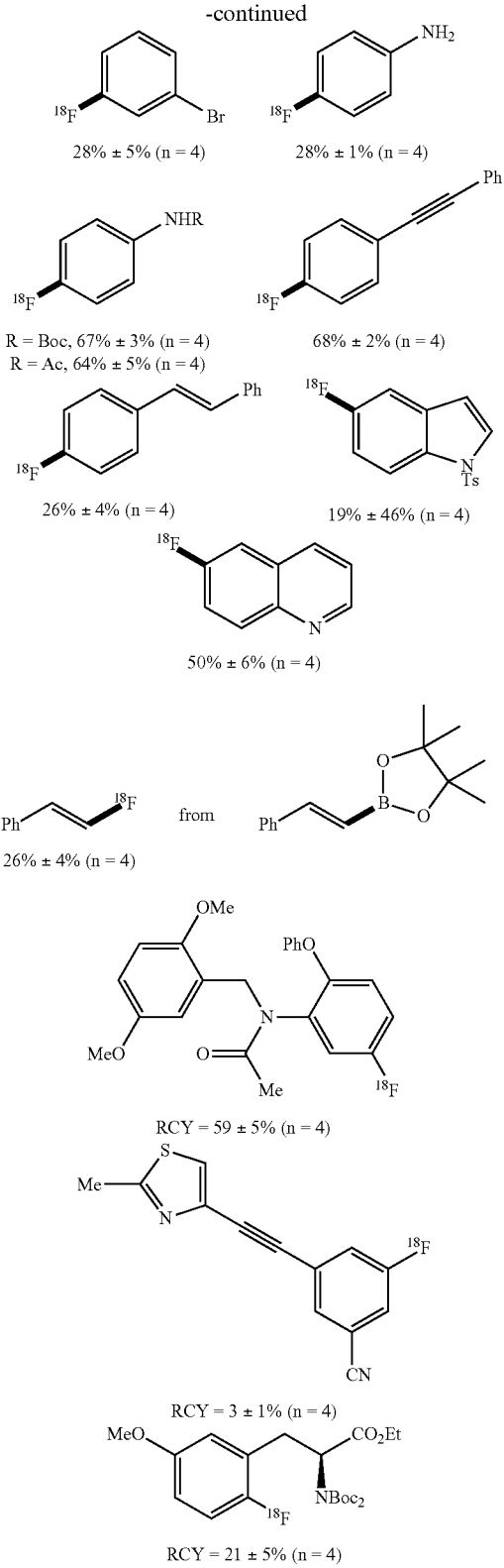

reach using this new radiochemistry inclusive of [18F]DAA1106 and 6-[18F]fluorotyrosine. The RCYs are indicated below each product.

Example 3—PET Biomarkers

Specific activity is an important consideration for new radiochemistry. The mass dose of the tool compound defines the extent of applications and dictates the level of toxicology required to support human use.

Ultimately, a major benefit of the invention is its amenability to late stage [18F]fluorination of well known biomarkers notoriously difficult to access from [18F]fluoride. The successful application of our method to electron-rich arenes such as phenol, aniline and veratrole derivatives offers tantalizing opportunities in [18F]biomarkers development. The method was directly applicable to the preparation of PET ligands and biomarkers used in the clinic. The translocator protein (TSPO) PET ligand [18F]DAA1106 was readily accessible in 59% RCY upon [18F]fluorination of the corresponding arylBpin precursor. This result is significant for imaging as TSPO is upregulated in activated microglia and can serve as a marker of neuroinflammation. [18F]3-(Fluoro)-5-((2-methylthiazol-4-yl)ethynyl)benzonitrile, an important high-affinity metabotropic glutamate subtype 5 receptor (mGluR5) ligand is also within reach and formed in 3% RCY. The protected 6-[18F]fluorotyrosine derivative was prepared in 21% RCY, Example 4—6-[18F]fluoro-L-DOPA

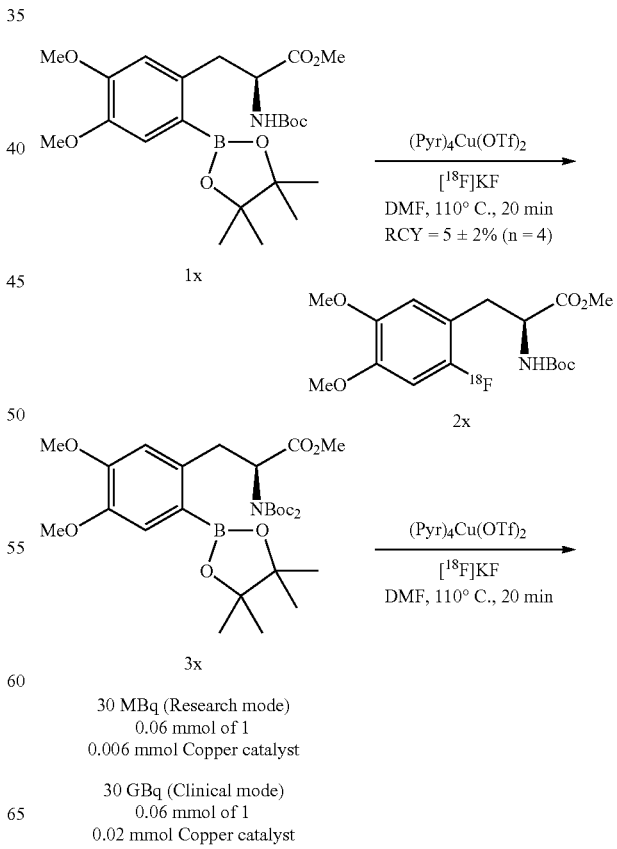

30 MBq (Research mode)
0.06 mmol of 1
0.006 mmol Copper catalyst

30 GBq (Clinical mode)
0.06 mmol of 1
0.02 mmol Copper catalyst

Table 2 shows Cu(II)-Mediated [18F]fluorination of aryl pinacol-derived boronic esters with [18F]fluoride. (A), Arenes and heteroarenes bearing a variety of functional groups are efficiently labelled with [18F]F. (B), [18F]fluoroalkenes are within reach applying the standard protocol to alkenylBPin. (C), A variety of known PET ligands are within

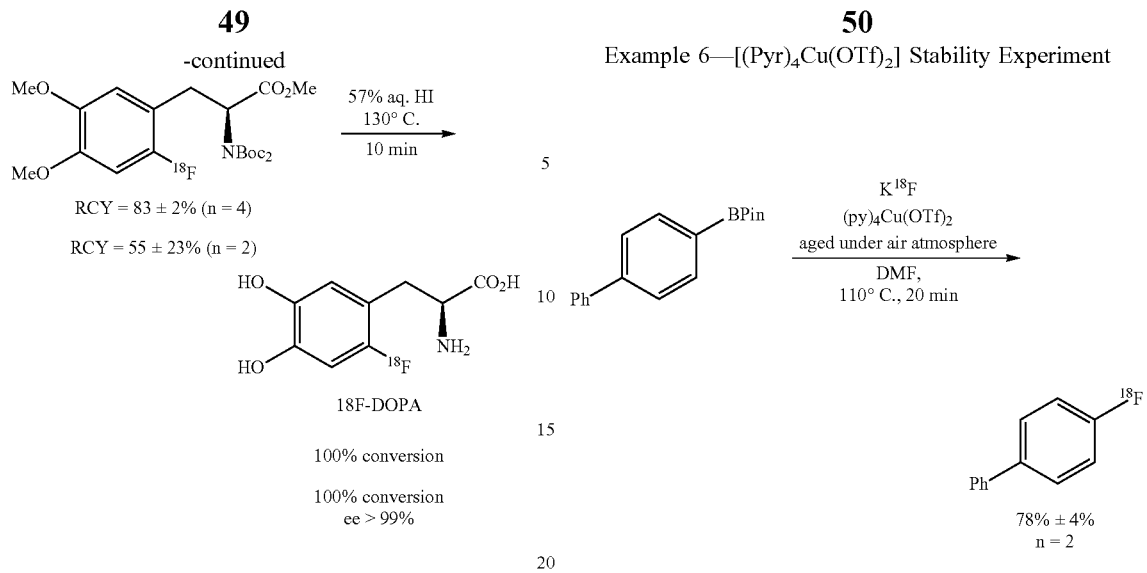

RCY = 83 ± 2% (n = 4)

RCY = 55 ± 23% (n = 2)

18F-DOPA

100% conversion

100% conversion
ee > 99%

To further demonstrate the high translational potential of nucleophilic [$^{18}$F]fluorination of arylBpin precursors, efforts were focused on the preparation of 6-[$^{18}$F]fluoro-L-DOPA, an iconic biomarker prepared in the clinic from [$^{18}$F]F$_2$, or requiring complex precursors that are neither shelf-stable nor readily accessible for nucleophilic [$^{18}$F]fluorination. Surprisingly, the [$^{18}$F]fluorination of arylBpin (S)-1x, a direct precursor of protected 6-[$^{18}$F]fluoro-L-DOPA proceeded in one stage applying the chosen reaction conditions. The desired protected intermediate [$^{18}$F](S)-2x was obtained in 5% RCY and its identity unambiguously confirmed by HPLC analysis.

The fluorination of the arylBpin (S)-3x produced the direct precursor of 6-[$^{18}$F]fluoro-L-DOPA in a RCY of up to 83%. This was then converted to 6-[$^{18}$F]fluoro-L-DOPA at 100% conversion with >99% ee.

Example 5—Reaction with Electron Deficient Substrate

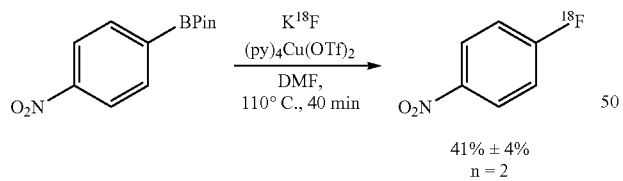

41% ± 4%
n = 2

To a V-vial containing (Pyr)$_4$Cu(OTf)$_2$ (3.6 mg, 0.0053 mmol), 4-nitrophenyl pinacol boronate (0.06 mmol) and a magnetic stirrer bar was added [$^{18}$F]KF/K$_{222}$ in MeCN. DMF (300 μL) was added via syringe. The sealed vial was heated at 110° C. for 40 minutes. The reaction was quenched by addition of water (200 μL). An aliquot was removed for analysis by radioTLC and HPLC for radiochemical yield and product identity. Analysis was performed using Gradient A with a Waters Nova-Pak C18 column (4 μm, 3.9×150 mm) at a flow rate 1 ml/min. RCY was increased more than two fold over identical reaction ran for 20 min (14% RCY).

Example 6—[(Pyr)$_4$Cu(OTf)$_2$] Stability Experiment

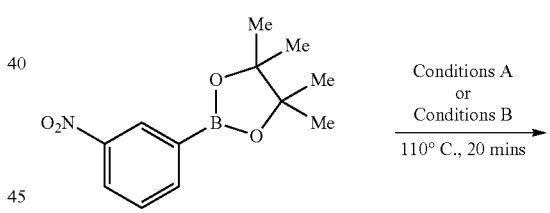

78% ± 4%
n = 2

General procedure was carried out using a sample of (Pyr)$_4$Cu(OTf)$_2$ (3.6 mg, 0.0053 mmol) which was left on a bench top open to air for 18 days. RCY were statically identical to samples stored under inert atmosphere (78%±4% compared with 74%±4%).

Example 7—Optimised $^{18}$F Radiolabelling Conditions

Using the process of the invention, different labelling conditions were tested as set out below.

Conditions A:
[$^{18}$F]KF/K$_{222}$
substrate (0.06 mmol),
[Cu(OTf)$_2$py$_4$] (0.0053 mmol)
solvent = dimethylformamide Conditions B:
[$^{18}$F]KF/K$_{222}$
substrate (0.02 mmol),
[Cu(OTf)$_2$py$_4$] (0.03 mmol)
solvent = dimethylacetamide

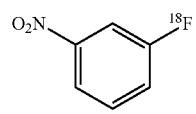

RCY = 14% ± 3% (n = 4)
RCY = 81% ± 3% (n = 2)

-continued

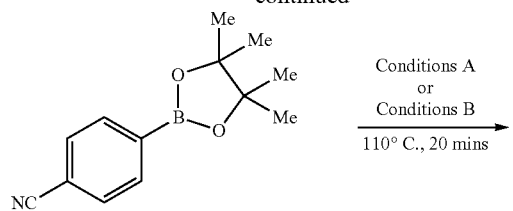

Conditions A or Conditions B
110° C., 20 mins

Conditions A:
[$^{18}$F]KF/K$_{222}$
substrate (0.06 mmol),
[Cu(OTf)$_2$py$_4$] (0.0053 mmol)
solvent = dimethylformamide Conditions B:
[$^{18}$F]KF/K$_{222}$
substrate (0.02 mmol),
[Cu(OTf)$_2$py$_4$] (0.03 mmol)
solvent = dimethylacetamide RCY = 39% ± 7% (n = 4)
RCY = 85% ± 1% (n = 2)

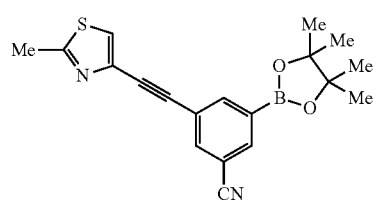

Conditions A or Conditions B
110° C., 20 mins

Conditions A:
[$^{18}$F]KF/K$_{222}$
substrate (0.06 mmol),
[Cu(OTf)$_2$py$_4$] (0.0053 mmol)
solvent = dimethylformamide Conditions B:
[$^{18}$F]KF/K$_{222}$
substrate (0.02 mmol),
[Cu(OTf)$_2$py$_4$] (0.03 mmol)
solvent = dimethylacetamide

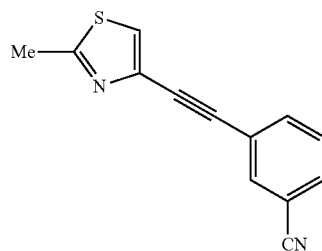

RCY = 3% ± 1% (n = 4)
RCY = 71% ± 2% (n = 5)

Example 8—$^{18}$F-Labelling of Heterocycles

The labelling of various heterocycles was performed using the process of the invention. The conditions and results are shown below.

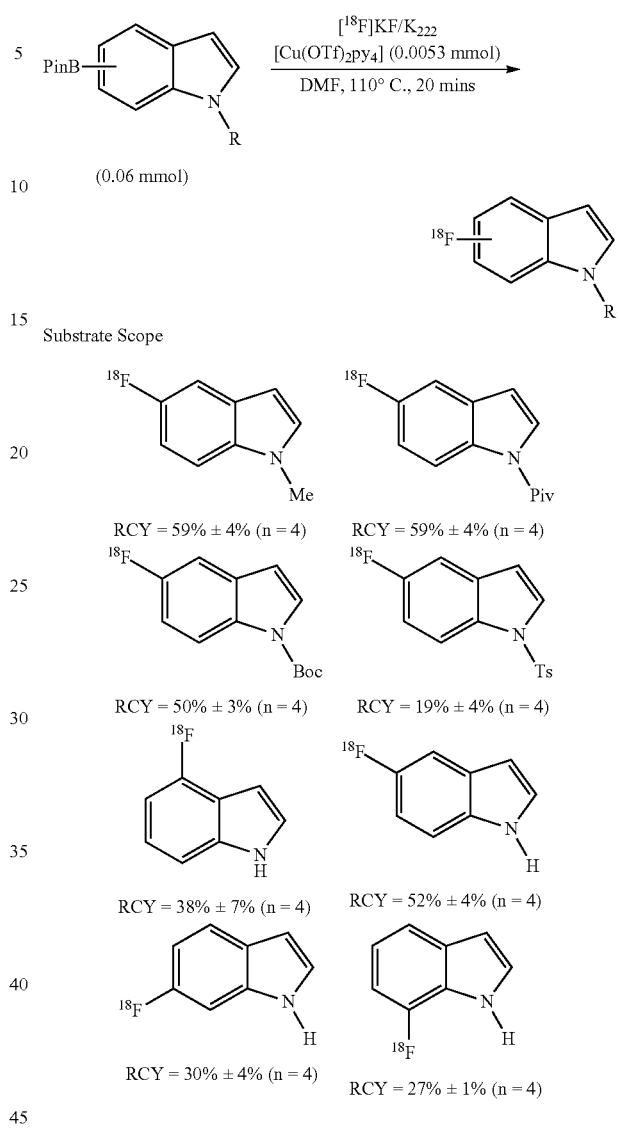

$^{18}$F-Labeling of Heterocycles

Substrate Scope

RCY = 59% ± 4% (n = 4)   RCY = 59% ± 4% (n = 4)
RCY = 50% ± 3% (n = 4)   RCY = 19% ± 4% (n = 4)
RCY = 38% ± 7% (n = 4)   RCY = 52% ± 4% (n = 4)
RCY = 30% ± 4% (n = 4)   RCY = 27% ± 1% (n = 4)

The process of the invention has been demonstrated to be effective for a variety of substrates.

The invention claimed is:

1. A process for producing an organic compound comprising an 18F atom, which process comprises treating an organoboron compound, which organoboron compound comprises a boron atom bonded to an sp2 hybridised carbon atom, with
   (i) 18F⁻; and
   (ii) (a) a copper (II) salt of formula [L$_n$Cu(OTf)$_2$] or (b) a copper (II) salt of formula Cu(OTf)$_2$ and L,
   wherein:
   n is an integer from 1 to 4; and
   each L is the same or different and is a ligand selected from the group consisting of:
   pyridine; pyridine substituted with one or more groups selected from C$_{1-6}$ alkyl and phenyl; quinoline; quinoline substituted with one or more groups selected from C$_{1-6}$ alkyl and phenyl; isoquinolone; isoquinoline substituted with one or more groups selected from $C_{1-6}$ alkyl and phenyl; pyrrole; pyrrole substituted with one or more groups selected from $C_{1-6}$ alkyl and phenyl; 2,3-benzopyrrole; 2,3-benzopyrrole substituted with one or more groups selected from $C_{1-6}$ alkyl and phenyl; N—$C_{1-6}$ alkylpyrazole; N—$C_{1-6}$ alkylpyrazole substituted with one or more groups selected from $C_{1-6}$ alkyl and phenyl; N—$C_{1-6}$ alkyl-1,2-benzopyrazole; N—$C_{1-6}$ alkyl-1,2-benzopyrazole substituted with one or more groups selected from $C_{1-6}$ alkyl and phenyl; N—$C_{1-6}$ alkyl-imidazole; N—$C_{1-6}$ alkyl-imidazole substituted with one or more groups selected from $C_{1-6}$ alkoxycarbonyl, $C_{1-6}$ alkyl and phenyl; pyridazine; pyridazine substituted with one or more groups selected from $C_{1-6}$ alkyl and phenyl; pyrimidine; pyrimidine substituted with one or more groups selected from $C_{1-6}$ alkyl and phenyl; benzopyrimidine; benzopyrimidine substituted with one or more groups selected from $C_{1-6}$ alkyl and phenyl; pyrazine; pyrazine substituted with one or more groups selected from $C_{1-6}$ alkyl and phenyl; benzopyrazine; benzopyrazine substituted with one or more groups selected from $C_{1-6}$ alkyl and phenyl; imidazo(1,2-b)pyridazine; imidazo(1,2-b)pyridazine substituted with one or more groups selected from $C_{1-6}$ alkoxy, $C_{1-6}$ alkyl and phenyl; [1,2,4]triazolo[1,5-a]pyridine; [1,2,4]triazolo[1,5-a]pyridine substituted with one or more groups selected from $C_{1-6}$ alkyl and phenyl; pyrazolo[1,5-a]pyridine; pyrazolo[1,5-a]pyridine substituted with one or more groups selected from $C_{1-6}$ alkyl and phenyl; 1H-pyrrolo[3,2-b]pyridine; 1H-pyrrolo[3,2-b]pyridine substituted with one or more groups selected from $C_{1-6}$ alkyl and phenyl; 1-$C_{1-6}$ alkyl-pyrrolo[2,3-b]pyridine; 1-$C_{1-6}$ alkyl-pyrrolo[2,3-b]pyridine substituted with one or more groups selected from $C_{1-6}$ alkyl and phenyl; 1-$C_{1-6}$ alkyl-1,2,3-triazole; 1-$C_{1-6}$ alkyl-1,2,3-triazole substituted with one or more groups selected from $C_{1-6}$ alkyl and phenyl; 1-$C_{1-6}$ alkyl-benzo[d][1,2,3]triazole; 1-$C_{1-6}$ alkyl-benzo[d][1,2,3]triazole substituted with one or more groups selected from $C_{1-6}$ alkyl and phenyl; 1-$C_{1-6}$ alkyl-1,2,4-triazole; 1-$C_{1-6}$ alkyl-1,2,4-triazole substituted with one or more groups selected from $C_{1-6}$ alkyl and phenyl; oxazole; oxazole substituted with one or more groups selected from $C_{1-6}$ alkyl and phenyl; benzoxazole; benzoxazole substituted with one or more groups selected from $C_{1-6}$ alkyl and phenyl; isoxazole; isoxazole substituted with one or more groups selected from $C_{1-6}$ alkyl and phenyl; benzisoxazole; benzisoxazole substituted with one or more groups selected from $C_{1-6}$ alkyl and phenyl; thiazole; thiazole substituted with one or more groups selected from $C_{1-6}$ alkyl and phenyl; benzothiazole; and benzothiazole substituted with one or more groups selected from $C_{1-6}$ alkyl and phenyl.

2. A process according to claim 1, wherein the organoboron compound comprises a boronic ester group, a boronic acid group, a borate group or a trifluoroborate group.

3. A process according to claim 1, wherein the copper compound is a compound of formula $[(Pyr)_4Cu^{II}(OTf)_2]$.

4. A process according to claim 1 wherein the organoboron compound is a compound of formula (II) or (III):

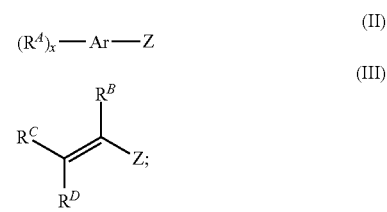

wherein:
Ar is an aryl ring or a heteroaryl ring;
each $R^A$ group is the same or different and is a group selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{3-20}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, aryloxy, haloalkyl, sulfonic acid, thiol, $C_{1-10}$ alkylthio, arylthio, sulfonyl, phosphoric acid, phosphate ester, phosphonic acid and phosphonate ester, wherein two or more $R^A$ groups may be bonded together to form one or more rings;
$R^B$, $R^C$, and $R^D$ are each independently selected from H, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{3-20}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, aryloxy, haloalkyl, sulfonic acid, thiol, $C_{1-10}$ alkylthio, arylthio, sulfonyl, phosphoric acid, phosphate ester, phosphonic acid and phosphonate ester, wherein two or more of $R^B$, $R^C$, and $R^D$ may be bonded together to form one or more rings;
Z is group selected from a boronic ester group, a boronic acid group, a borate group or a trifluoroborate group; and
x is an integer from 0 to 5.

5. A process according to claim 4, wherein Z is a group of formula (IV):

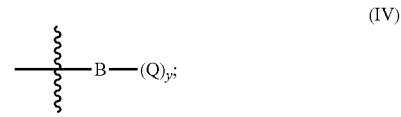

wherein:
each Q is the same or different and is a group selected from —$OR^E$, —OH, and fluoride;
each $R^E$ is the same or different and is a group selected from substituted or unsubstituted $C_{1-10}$ alkyl, substituted or unsubstituted $C_{2-10}$ alkenyl, substituted or unsubstituted $C_{2-10}$ alkynyl, substituted or unsubstituted C$_{3-10}$ cycloalkyl, substituted or unsubstituted heterocyclyl, substituted or unsubstituted aryl, substituted or unsubstituted heteroaryl, acyl, ester, amido, and haloalkyl, wherein two or more R$^E$ groups may be bonded together to form one or more rings; and
y is 2 or 3.

6. A process according to claim 5, wherein Z is a group of formula —B(OR$^E$)$_2$.

7. A process according to claim 4, wherein Z is a group of formula (V):

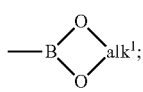

(V)

wherein alk$^1$ is a substituted or unsubstituted alkylene group, optionally interrupted with one or more —O— or —N(R$^F$)— groups, wherein R$^F$ is a group selected from H, substituted or unsubstituted C$_{1-10}$ alkyl, acyl, ester, amido and acyloxy.

8. A process according to claim 4, wherein Z is a group of formula (VI) or (VII):

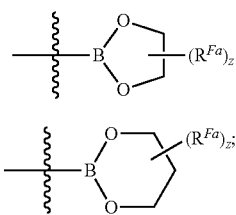

(VI)

(VII)

wherein:
each R$^{Fa}$ is a group independently selected from substituted or unsubstituted C$_{1-10}$ alkyl, substituted or unsubstituted C$_{2-10}$ alkenyl, substituted or unsubstituted C$_{2-10}$ alkynyl, substituted or unsubstituted C$_{3-10}$ cycloalkyl, substituted or unsubstituted heterocyclyl, substituted or unsubstituted aryl, substituted or unsubstituted heteroaryl, cyano, amino, C$_{1-10}$ alkylamino, di(C$_{1-10}$)alkylamino, arylamino, diarylamino, arylalkylamino, amido, acylamido, hydroxy, oxo, halo, carboxy, ester, acyl, acyloxy, C$_{1-10}$ alkoxy, aryloxy, haloalkyl, sulfonic acid, thiol, C$_{1-10}$ alkylthio, arylthio, sulfonyl, phosphoric acid, phosphate ester, phosphonic acid and phosphonate ester; and
z is an integer from 0 to 6.

9. A process according to claim 4, wherein Z is a group selected from

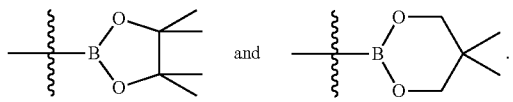

10. A process according to claim 4, wherein Ar is a ring selected from phenyl, pyridinyl, pyridonyl, pyrimidinyl, pyrimidonyl, pyrimidinedionyl, pyrrolyl, oxazolyl, thiazolyl, and imidazolyl.

11. A process according to claim 4, wherein Ar is a ring selected from phenyl, pyridinyl, pyridonyl, pyrimidinyl, pyrimidonyl, and pyrimidinedionyl.

12. A process according to claim 4, wherein the organoboron compound is a compound of formula (VIII), (IX), (X), or (XI):

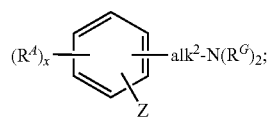

(VIII)

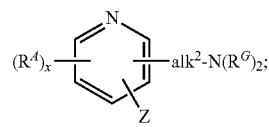

(IX)

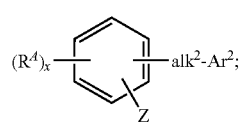

(X)

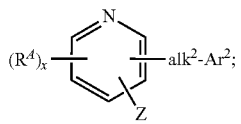

(XI)

wherein:
Ar$^2$ is a substituted or unsubstituted aryl group or a substituted or unsubstituted heteroaryl group;
alk$^2$ is a single bond or a substituted or unsubstituted C$_{1-20}$ alkylene group, a substituted or unsubstituted C$_{2-20}$ alkenylene group, a substituted or unsubstituted C$_{2-20}$ alkynylene group, wherein alk$^2$ may be optionally interrupted with one or more —O— or —N(R$^F$)— groups, wherein R$^F$ is a group selected from H, substituted or unsubstituted C$_{1-10}$ alkyl, acyl, ester, and amido;
each R$^A$ group is the same or different and is a group selected from substituted or unsubstituted C$_{1-20}$ alkyl, substituted or unsubstituted C$_{2-20}$ alkenyl, substituted or unsubstituted C$_{2-20}$ alkynyl, substituted or unsubstituted C$_{3-20}$ cycloalkyl, substituted or unsubstituted heterocyclyl, substituted or unsubstituted aryl, substituted or unsubstituted heteroaryl, cyano, amino, C$_{1-10}$ alkylamino, di(C$_{1-10}$)alkylamino, arylamino, diarylamino, arylalkylamino, amido, acylamido, hydroxy, halo, carboxy, ester, acyl, acyloxy, C$_{1-20}$ alkoxy, aryloxy, haloalkyl, sulfonic acid, thiol, C$_{1-10}$ alkylthio, arylthio, sulfonyl, phosphoric acid, phosphate ester, phosphonic acid and phosphonate ester, or two or more R$^A$ groups may be bonded together to form one or more rings;
each R$^G$ is the same or different and is group selected from H, substituted or unsubstituted C$_{1-20}$ alkyl, substituted or unsubstituted C$_{2-20}$ alkenyl, substituted or unsubstituted C$_{2-20}$ alkynyl, substituted or unsubstituted C$_{3-20}$ cycloalkyl, substituted or unsubstituted heterocyclyl, substituted or unsubstituted aryl, substituted or unsubstituted heteroaryl, ester, acylamido, acyl, and acyloxy, or both R$^G$ groups together form a substituted or unsubstituted heterocyclyl group or a substituted or unsubstituted heteroaryl group;
x is an integer from 0 to 4;
and Z is a group selected from a boronic ester group, a boronic acid group, a borate group or a trifluoroborate group.

13. A process according to claim 12 wherein the organoboron compound is a compound of formula (XII), (XIII) or (XV):

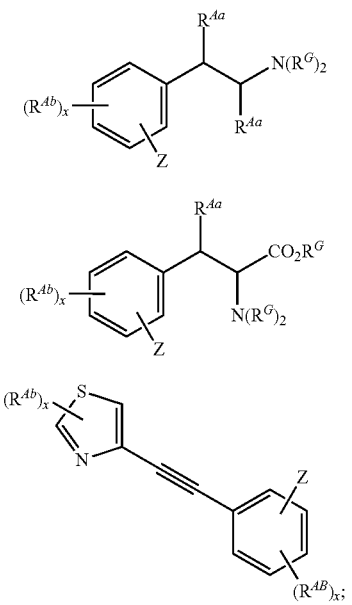

wherein:
each $R^{Aa}$ group is the same or different and is a group selected from H, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{3-20}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, aryloxy, haloalkyl, sulfonic acid, thiol, $C_{1-10}$ alkylthio, arylthio, sulfonyl, phosphoric acid, phosphate ester, phosphonic acid and phosphonate ester, wherein two or more $R^{Aa}$ groups may be bonded together to form one or more rings;
each $R^{Ab}$ group is the same or different and is a group selected from substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{3-20}$ cycloalkyl, substituted or unsubstituted heterocyclyl, substituted or unsubstituted aryl, substituted or unsubstituted heteroaryl, cyano, amino, $C_{1-10}$ alkylamino, di($C_{1-10}$)alkylamino, arylamino, diarylamino, arylalkylamino, amido, acylamido, hydroxy, halo, carboxy, ester, acyl, acyloxy, $C_{1-20}$ alkoxy, aryloxy, haloalkyl, sulfonic acid, thiol, $C_{1-10}$ alkylthio, arylthio, sulfonyl, phosphoric acid, phosphate ester, phosphonic acid and phosphonate ester, wherein two or more $R^{Ab}$ groups may be bonded together to form one or more rings;
each $R^G$ is the same or different and is group selected from H, substituted or unsubstituted $C_{1-20}$ alkyl, substituted or unsubstituted $C_{2-20}$ alkenyl, substituted or unsubstituted $C_{2-20}$ alkynyl, substituted or unsubstituted $C_{3-20}$ cycloalkyl, substituted or unsubstituted heterocyclyl, substituted or unsubstituted aryl, substituted or unsubstituted heteroaryl, acylamido, acyl, and acyloxy, or both $R^G$ groups together form a substituted or unsubstituted heterocyclyl group or a substituted or unsubstituted aryl group;
each x is independently an integer from 0 to 4; and
Z is a group selected from a boronic ester group, a boronic acid group, a borate group or a trifluoroborate group.

14. A process according to claim 4, wherein the organoboron compound is a compound of formula (XVII) or (XVIII):

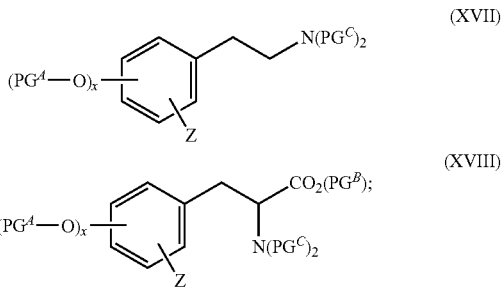

wherein:
each $PG^A$ is independently H or an alcohol protecting group;
$PG^B$ is H or a carboxylic acid protecting group;
each $PG^C$ is independently H or an amine protecting group;
x is an integer from 0 to 4; and
Z is a group selected from a boronic ester group, a boronic acid group, a borate group or a trifluoroborate group.

15. A process according to claim 14 wherein the organoboron compound is a compound of formula (XIX), (XX) or (XXI):

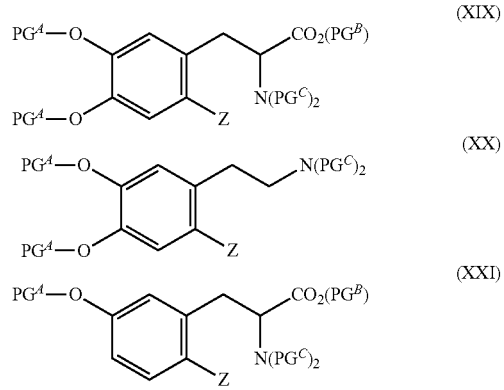

wherein:
each $PG^A$ is independently H or an alcohol protecting group;
$PG^B$ is H or a carboxylic acid protecting group;
each $PG^C$ is independently H or an amine protecting group; and
Z is a group selected from a boronic ester group, a boronic acid group, a borate group or a trifluoroborate group.

16. A process according to claim 14 wherein:
each $PG^A$ is independently H or an alcohol protecting group selected from substituted or unsubstituted $C_{1-10}$ alkyl, substituted or unsubstituted —C(O)—$C_{1-10}$ alkyl, substituted or unsubstituted —$C_{1-10}$ alkylene-O—$C_{1-10}$ alkyl optionally wherein the $C_{1-10}$ alkylene group and $C_{1-10}$ alkyl group may be bonded together to form a ring, and substituted or unsubstituted alkyl) silyl;

$PG^B$ is H or a carboxylic acid protecting group selected from substituted or unsubstituted $C_{1-10}$ alkyl, substituted or unsubstituted —C(O)—$C_{1-10}$ alkyl, and substituted or unsubstituted tri($C_{1-10}$ alkyl) silyl; and each $PG^C$ is independently H or an amine protecting group selected from substituted or unsubstituted $C_{1-10}$ alkyl, substituted or unsubstituted —C(O)—$C_{1-10}$ alkyl, substituted or unsubstituted —C(O)—O—$C_{1-10}$ alkyl, and substituted or unsubstituted —S(O)$_2$-aryl.

17. A process according to claim 14 wherein:
each $PG^A$ is independently H or a group selected methyl, ethyl, tert-butyl, benzyl, p-methoxybenzyl, trityl, acetyl, benzoyl, pivaloyl, methoxymethyl, methoxyethoxymethyl, methoxytrityl, dimethoxytrityl, tetrahydrofuranyl, tetrahydropyranyl, trimethylsilyl, tert-butyldimethylsilyl, tri-iso-propyl silyloxymethyl, and tri-iso-propyl silyl;

$PG^B$ is H or a group selected from methyl, ethyl, tert-butyl, benzyl, p-methoxybenzyl, trityl, trimethyl silyl, tert-butyldimethyl silyl, tri-iso-propyl silyloxymethyl, and tri-iso-propyl silyl; and each $PG^C$ is independently H or a group selected from carbobenzyloxy (Cbz), p-methoxybenzyl carbonyl (Moz), tert-butyloxycarbonyl (Boc), 9-fluorenylmethyloxycarbonyl (FMOC), acetyl, benzoyl, benzyl, p-methoxybenzyl (PMB), 3,4-dimethoxylbenzyl (DMPM), p-methoxyphenyl (PMP), tosyl (Ts) and Nosyl.

18. A process according to claim 1, wherein the organoboron compound is a compound of formula (XXII), (XXIII), (XXIIA) or (XXIIIA):

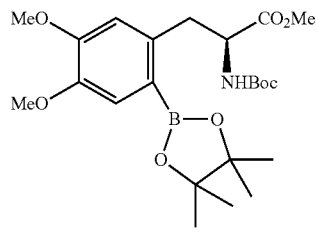
(XXII)

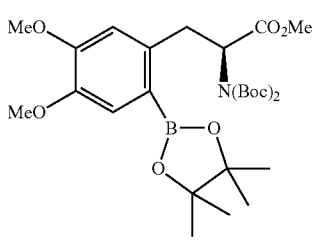
(XXIII)

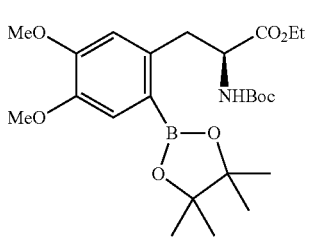
(XXIIA)

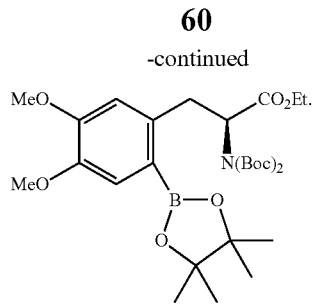
(XXIIIA)

19. A process according to claim 1, wherein the ratio of the amount of the organoboron compound to the amount of the copper compound is from 1:1 to 40:1, preferably from 3:1 to 20:1.

20. A process according to claim 1, wherein the process is carried out in the presence of a solvent selected from dimethyl formamide and acetonitrile.

21. A process according to claim 1, wherein the organoboron compound, the copper compound and the $^{18}F^-$ are heated to a temperature of from 80 to 150° C.

22. A process according to claim 1, wherein the organic compound comprising an $^{18}F$ atom is a compound of formula (II), (III), (VIII), (IX), (X), (XI), (XII), (XIII), (XV), (XVII), (XVIII), (XIX), (XX), (XXI), (XXII), (XXIIA), (XXIII) or (XXIIIA), except wherein Z is replaced with $^{18}F$.

23. A process according to claim 1, wherein the organic compound comprising an $^{18}F$ atom is a compound of formula (XXIV), (XXV), (XXVI), (XXVII), or (XXVIII):

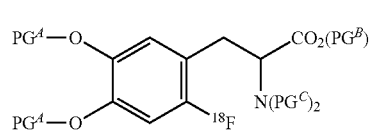
(XXIV)

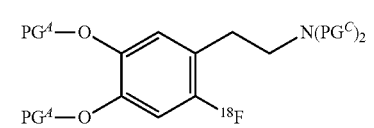
(XXV)

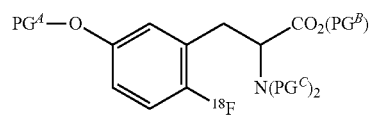
(XXVI)

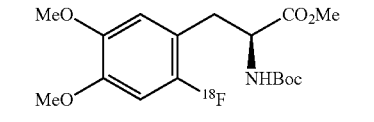
(XXVII)

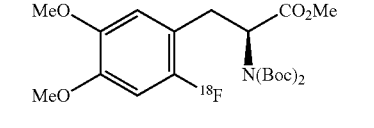
(XXVIII)

wherein
each $PG^A$ is independently H or an alcohol protecting group;
$PG^B$ is H or a carboxylic acid protecting group; and
each $PG^C$ is independently H or an amine protecting group.

24. A process according to claim 1, wherein the process further comprises a step of removing one or more protecting groups from the compound comprising an $^{18}F$ atom to produce a deprotected product.

25. A process according to claim 24, wherein the deprotected product is a PET ligand.
26. A process according to claim 24, wherein the deprotected product is a compound of formula (XXX), (XXXII), (XXXIII) or (XXXIV):
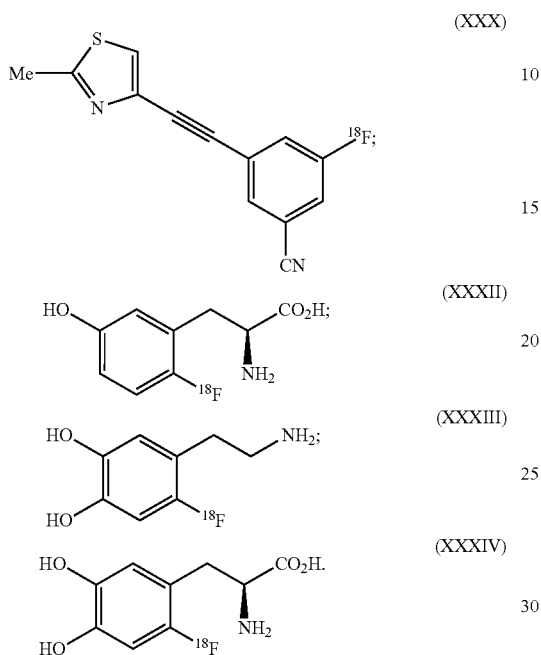
* * * * *

UNITED STATES PATENT AND TRADEMARK OFFICE
CERTIFICATE OF CORRECTION

PATENT NO.       : 10,287,220 B2
APPLICATION NO.  : 15/127599
DATED            : May 14, 2019
INVENTOR(S)      : V. Gouverneur et al.

Page 1 of 1

It is certified that error appears in the above-identified patent and that said Letters Patent is hereby corrected as shown below:

In the Claims

| Column | Line | Error |
|---|---|---|
| 59 (Claim 16, Line 8) | 4 | "alkyl)" should read --tri($C_{1-10}$ alkyl)-- |

Signed and Sealed this
Twenty-fourth Day of September, 2019

Andrei Iancu
*Director of the United States Patent and Trademark Office*